US011864878B2

(12) United States Patent
Duval et al.

(10) Patent No.: US 11,864,878 B2
(45) Date of Patent: Jan. 9, 2024

(54) DEVICES AND METHODS FOR DETERMINING BLOOD FLOW AROUND A BODY LUMEN

(71) Applicant: Boston Scientific Scimed, Inc., Maple Grove, MN (US)

(72) Inventors: George Wilfred Duval, Sudbury, MA (US); Michael Y. Ko, Waltham, MA (US); James Weldon, Newton, MA (US); Namita M. Kallur, Hayward, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 308 days.

(21) Appl. No.: 17/180,264

(22) Filed: Feb. 19, 2021

(65) Prior Publication Data
US 2021/0169352 A1 Jun. 10, 2021

Related U.S. Application Data

(63) Continuation of application No. 16/011,925, filed on Jun. 19, 2018, now Pat. No. 10,959,627.
(Continued)

(51) Int. Cl.
*A61B 5/026* (2006.01)
*A61B 5/107* (2006.01)
(Continued)

(52) U.S. Cl.
CPC .......... *A61B 5/0261* (2013.01); *A61B 5/0086* (2013.01); *A61B 5/0205* (2013.01);
(Continued)

(58) Field of Classification Search
CPC ...... A61B 5/0084–0086; A61B 5/0261; A61B 5/14551–14557; A61B 5/1459;
(Continued)

(56) References Cited

U.S. PATENT DOCUMENTS 6,866,655 B2  3/2005  Hackett
7,231,243 B2  6/2007  Tearney et al.
(Continued)

FOREIGN PATENT DOCUMENTS

EP   1496805 B1   1/2012
EP   3095379 A1   11/2016
(Continued)

OTHER PUBLICATIONS

Volceka, K., et al. "Development of a non-invasive LED based device for adipose tissue thickness measurements in vivo." Biophotonics: Photonic Solutions for Better Health Care III. vol. 8427. International Society for Optics and Photonics, 2012.
(Continued)

*Primary Examiner* — Thaddeus B Cox
(74) *Attorney, Agent, or Firm* — Bookoff McAndrews, PLLC

(57) ABSTRACT

A system may include an expandable member, and a plurality of sensors disposed on an outer surface of the expandable member and circumferentially spaced apart from one another, wherein each of the plurality of sensors includes a first emitter configured to emit light of a first wavelength, and a detector configured to detect light, and a controller coupled to the plurality of sensors.

20 Claims, 17 Drawing Sheets

Related U.S. Application Data

(60) Provisional application No. 62/522,168, filed on Jun. 20, 2017.

(51) Int. Cl.
*A61B 5/1455* (2006.01)
*A61B 5/00* (2006.01)
*A61B 5/0205* (2006.01)
*A61B 5/349* (2021.01)
*A61B 5/027* (2006.01)
*A61B 5/0295* (2006.01)
*A61B 5/0285* (2006.01)

(52) U.S. Cl.
CPC ........ *A61B 5/1072* (2013.01); *A61B 5/14551* (2013.01); *A61B 5/349* (2021.01); *A61B 5/4255* (2013.01); *A61B 5/6853* (2013.01); *A61B 5/6858* (2013.01); *A61B 5/027* (2013.01); *A61B 5/0285* (2013.01); *A61B 5/0295* (2013.01); *A61B 5/4216* (2013.01); *A61B 5/4233* (2013.01); *A61B 5/4238* (2013.01); *A61B 2562/043* (2013.01)

(58) Field of Classification Search
CPC ...... A61B 5/1072; A61B 5/1075–1076; A61B 2562/043
See application file for complete search history.

(56) References Cited

U.S. PATENT DOCUMENTS

| | | | |
|---|---|---|---|
| 8,052,597 | B2 | 11/2011 | Boulais |
| 9,339,221 | B1* | 5/2016 | Heaton, II ............. A61B 5/742 |
| 2002/0026121 | A1 | 2/2002 | Kan |
| 2008/0045842 | A1 | 2/2008 | Furnish |
| 2012/0209086 | A1 | 8/2012 | Beute |
| 2014/0316254 | A1* | 10/2014 | Eversull ............... A61B 5/6885 |
| | | | 600/424 |
| 2015/0122870 | A1 | 5/2015 | Zemlok et al. |
| 2015/0238088 | A1* | 8/2015 | Hufnagel ............. A61B 5/4836 |
| | | | 600/476 |
| 2016/0310027 | A1 | 10/2016 | Han |
| 2017/0319076 | A1* | 11/2017 | McCarthy ............. A61B 5/746 |
| 2018/0110423 | A1 | 4/2018 | Presura et al. |

FOREIGN PATENT DOCUMENTS

| | | |
|---|---|---|
| WO | 2008/011163 A2 | 1/2008 |
| WO | 2011/150379 A2 | 12/2011 |

OTHER PUBLICATIONS

Ho, Dong-Su, et al. "Optical skin-fat thickness measurement using miniaturized chip LEDs: A preliminary human study." Journal of the Optical Society of Korea 13.3 (2009): 304-309.

Extended European search report in corresponding European Application No. 23161073.4, dated Apr. 18, 2023 (7 pages).

* cited by examiner

DEVICES AND METHODS FOR DETERMINING BLOOD FLOW AROUND A BODY LUMEN

CROSS-REFERENCE TO RELATED APPLICATION(S)

This patent application is a continuation of U.S. patent application Ser. No. 16/011,925, filed on Jun. 19, 2018, now U.S. Pat. No. 10,959,627, which claims the benefit under 35 U.S.C. § 119 to U.S. Provisional Application No. 65/522,168, filed on Jun. 20, 2017, the entireties of which are incorporated by reference.

TECHNICAL FIELD

Implementations of the present disclosure relate to devices and methods for determining blood flow around a body lumen, and more specifically, an indicator for identifying inflamed regions of the gastrointestinal tract.

INTRODUCTION

Inflammatory Bowel Disease (IBD) is a disease that progresses from the mucosal lining of the small bowel or/and colon through the entire bowel/colon wall. Currently, the use of magnetic resonance imaging (MRI) slices as a non-invasive imaging technique for diagnosing IBD is limited by resolution, and does not provide real-time blood flow. Coherence tomography (CT) is another approach, but is not suitable for patients with certain gastrointestinal diseases because the requirement for multiple imaging sessions over time increases the risk of cancer for the patient. Other challenges include subjective severity in scoring from doctor to doctor, diagnosis through elimination, increased patient risk for cancer due to monitoring progression with repetitive CT-scans, and the unavailability of and lack of standardization associated with color enhanced ultrasound.

SUMMARY

In one implementation, the disclosure is directed to a system including an expandable member, and a plurality of sensors disposed on an outer surface of the expandable member and circumferentially spaced apart from one another, wherein each of the plurality of sensors includes a first emitter configured to emit light of a first wavelength, and a detector configured to detect light, and a controller communicatively coupled to the plurality of sensors. The controller may be configured to, from at least one detector, receive along a first short vector, a measurement of light intensity over time of light, reflected off of body tissue, at the first wavelength and originating from a first emitter from a same sensor; from at least one detector, receive along a first long vector, a measurement of light intensity over time of light, reflected off of body tissue, at the first wavelength and originating from a first emitter from a circumferentially adjacent sensor; calculate separate perfusion indexes corresponding to measured light intensity over time of each first short vector and each first long vector; and initiate the display of the separate perfusion indexes corresponding to measured light intensity over time of each first short vector and each first long vector.

Each of the plurality of sensors may include a second emitter configured to emit light of a second wavelength that is different than the first wavelength, wherein the controller is further configured to from each detector, receive along a second short vector, a measurement of light intensity over time of light, reflected off of body tissue, at the second wavelength and originating from a second emitter from a same sensor; from each detector, receive along a second long vector, a measurement of light intensity over time of light, reflected off of body tissue, at the second wavelength and originating from a second emitter from a circumferentially adjacent sensor; calculate separate perfusion indexes corresponding to each second short vector and each second long vector; and cause the display of the calculated separate perfusion indexes corresponding to each second short vector and each second long vector. The second emitter may be configured to emit light of a third wavelength different than the first wavelength and the second wavelength, wherein the controller is further configured to: from each detector, receive along a third short vector, a measurement of light intensity over time of light, reflected off of body tissue, at the third wavelength and originating from a second emitter from a same sensor; from each detector, receive along a third long vector, a measurement of light intensity over time of light, reflected off of body tissue, at the third wavelength and originating from a second emitter from a circumferentially adjacent sensor; calculate separate perfusion indexes corresponding to each third short vector and each third long vector; and cause the display of the calculated separate perfusion indexes corresponding to each third short vector and each third long vector. The controller may be further configured to, from each detector, receive along two third long vectors, measurements of light intensity over time of light, reflected off of body tissue, at the third wavelength and originating from second emitters of two different circumferentially adjacent sensors. The third wavelength may be infrared light. The controller may be further configured to, from each detector, receive along two second long vectors, measurements of light intensity over time of light, reflected off of body tissue, at the second wavelength and originating from second emitters of two different circumferentially adjacent sensors. The second wavelength may be visible red light. The controller may be further configured to, from each detector, receive along two first long vectors, measurements of light intensity over time of light, reflected off of body tissue, at the first wavelength and originating from first emitters of two different circumferentially adjacent sensors. The first wavelength may be visible green light. The system may include an ECG assembly coupled to the controller and configured to measure ECG signals. The controller may be further configured to: while calculating each perfusion index, synchronize in time, measured light intensity from each vector with a measurement from the ECG assembly to determine pulse transit time and perfusion intensity; and use the pulse transit time and the perfusion intensity to calculate a respective perfusion index corresponding to each vector. The controller may be configured to receive a measurement of light intensity over time along only one first short vector or first long vector at any given time. The plurality of sensors may include four circumferentially spaced apart sensors. Each detector may be longitudinally aligned with each other detector. Each first emitter may be longitudinally aligned with each other first emitter.

In another implementation, the disclosure is directed to a method for determining blood flow surrounding a body lumen, the method comprising: receiving, at separate times with a detector: a measurement of light intensity over time of light, reflected off of body tissue, at a first wavelength and originating from an emitter from a sensor circumferentially aligned with the detector; and a measurement of light intensity over time of light, reflected off of body tissue, at the first wavelength and originating from an emitter from a sensor circumferentially offset from the detector; calculating separate perfusion indexes corresponding to each measurement; and displaying the separate perfusion indexes.

In yet another implementation, the disclosure is directed to a method for determining blood flow surrounding a body lumen using a plurality of sensors, the method comprising: receiving, with a detector at each sensor, a measurement of light intensity over time of light, reflected off of body tissue, at a first wavelength and originating from a first emitter from a same sensor as the detector; receiving, with a detector at each sensor, a measurement of light intensity over time of light, reflected off of body tissue, at a first wavelength and originating from a first emitter from a sensor circumferentially adjacent to the detector; calculating separate perfusion indexes based on each measurement; and displaying the separate perfusion indexes.

The body lumen may be in a gastrointestinal tract. Only one measurement may be received at any given time. Each measurement may be taken while the plurality of sensors are in a same location within the body lumen.

In yet another implementation, the disclosure is directed to a medical device including a catheter; an optical sensor disposed at or adjacent to a distal end of the catheter, the optical sensor including a photodetector and one or more emitters, the photodetector and each of the one or more emitters of the optical sensor being disposed linearly along a longitudinal axis of the catheter; and a controller disposed within the catheter, the controller being configured to determine a thickness of tissue adjacent to the optical sensor based on input from the optical sensor.

BRIEF DESCRIPTION OF THE DRAWINGS

The accompanying drawings, which are incorporated in and constitute a part of this specification, illustrate various implementations and together with the description, serve to explain the principles of the disclosed implementations.

DETAILED DESCRIPTION

Reference will now be made in detail to implementations of the present disclosure, which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body. In the discussion that follows, relative terms such as "about," "substantially," "approximately," etc. are used to indicate a possible variation of ±10% in a stated numeric value.

Implementations of the present disclosure may provide a low-cost imaging solution for determining the severity of various gastrointestinal diseases. In some implementations, the data collected and displayed to a physician or clinician may be robust enough to enable differentiation of ulcerative colitis from Chrohn's disease.

Figure 1:
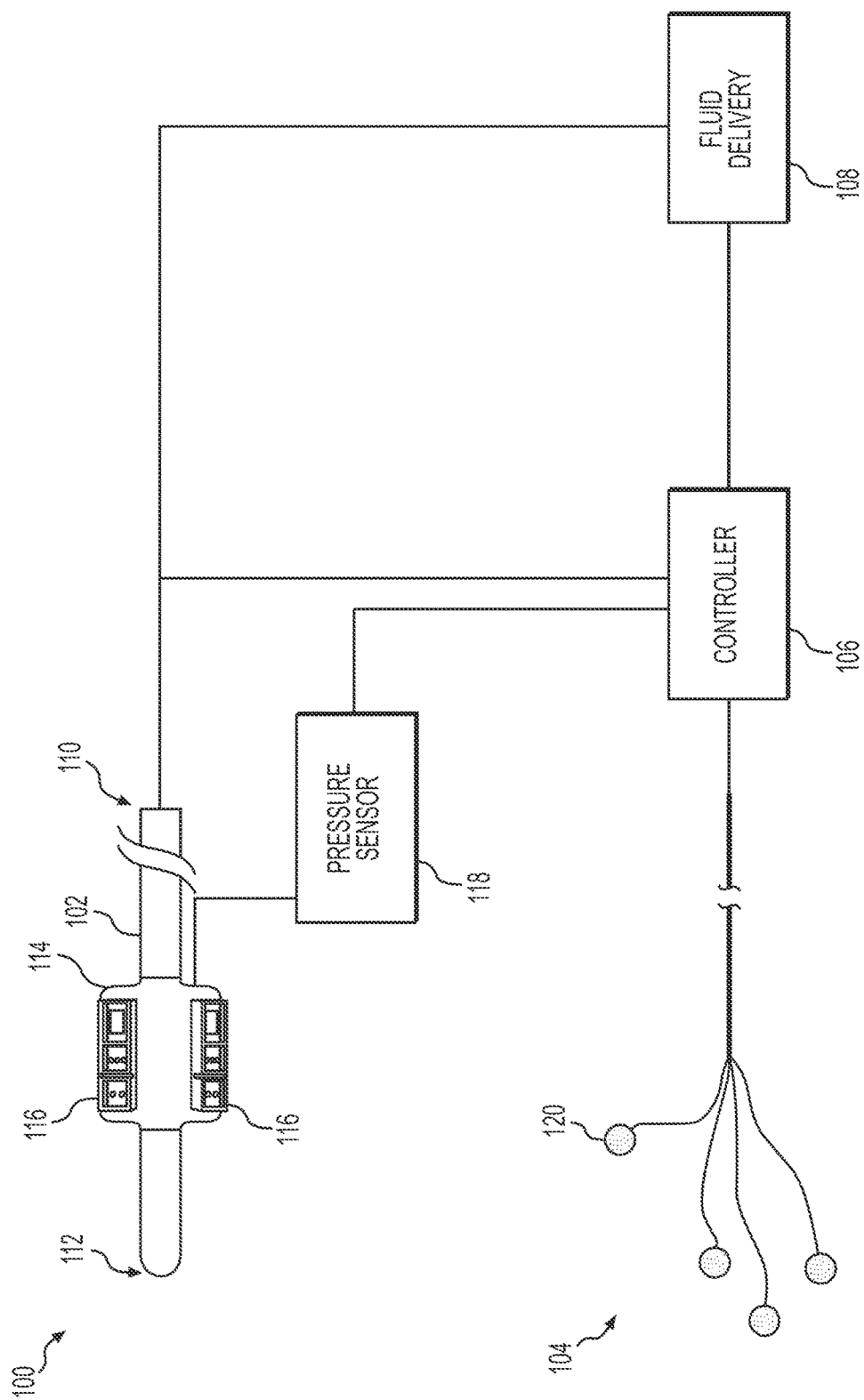
FIG. 1 is a schematic view of a perfusion measurement system, according to an implementation of the present disclosure.
Figure 2:
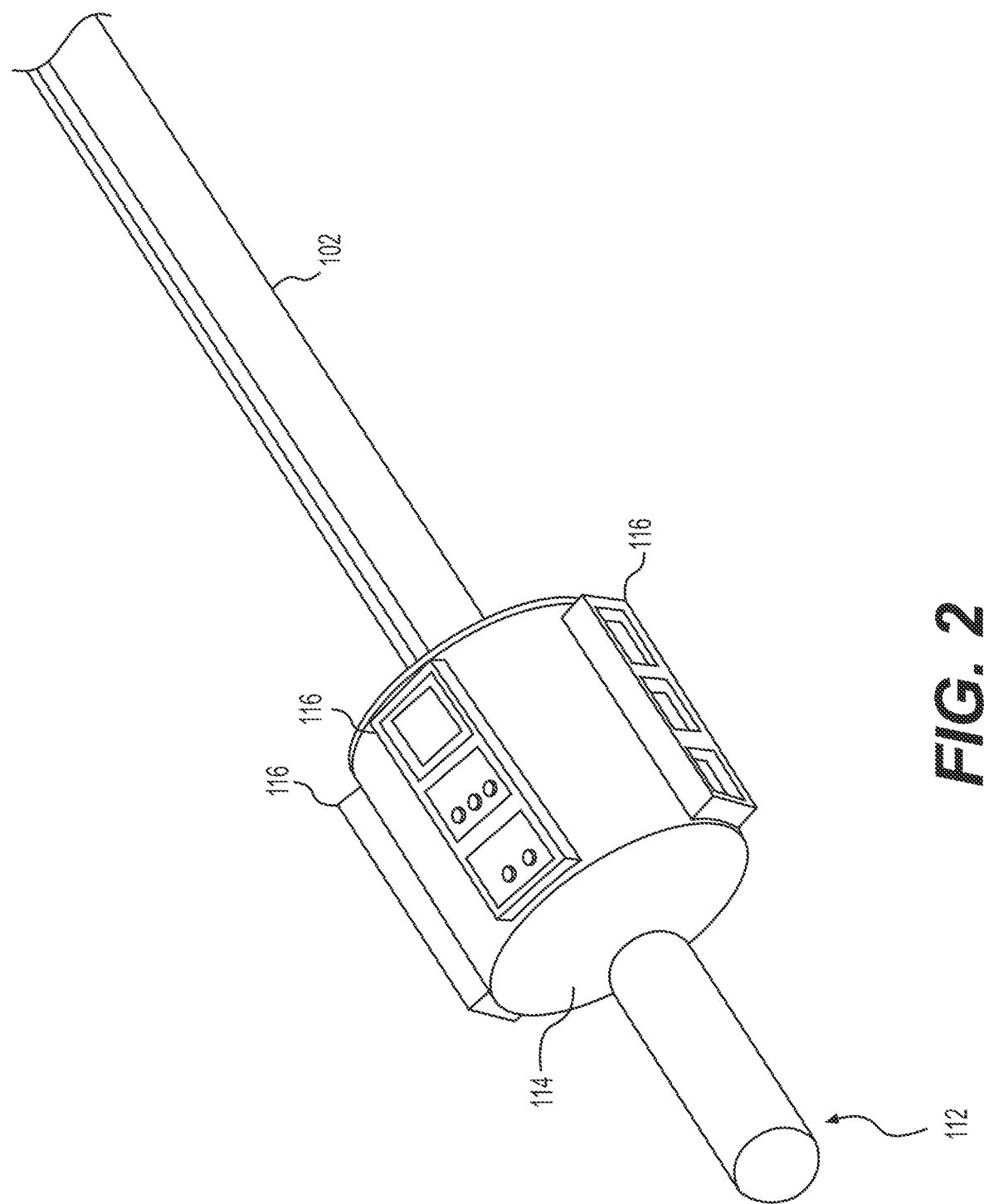
FIG. 2 is a perspective view of an expandable member with a plurality of optical sensors.

Referring to FIG. 1, a system 100 may include a catheter 102, an electrocardiogram (ECG) lead assembly 104, controller 106, and a fluid delivery device 108.

Catheter 102 may extend from a proximal end 110 toward a distal end 112, and may include an expandable member 114 at or adjacent distal end 112. Expandable member 114 may be a compliant or semi-compliant balloon configured to inflate and deflate via a fluid conveyed by fluid delivery device 108. In other implementations, expandable member 114 could be an expandable mesh or an expandable basket with a plurality of radially expandable basket legs. As explained in further detail below, one or more sensors may be coupled to expandable member 114 for measuring blood flow, pressure (e.g., pressure sensor 118), and/or impedance within a gastrointestinal tract of a patient. Pressure sensor 118 may be configured to measure pressure within expandable member 114, and to measure intra-abdominal pressure (IAP) within the body lumen when expandable member 114 is deflated. In embodiments where expandable member 114 is a balloon, pressure sensor 118 may be integral or otherwise coupled to an inflating pump. In embodiments where expandable member 114 is a mesh, a miniature integrated MEMS sensor may be used to measure pressure, and could be placed in the same plane as one or more optical sensors. Controller 106 may evaluate signals from pressure sensor 118 to control inflation and deflation of expandable member 114, so as not to cause any vascular restriction or accidental occlusion. Pressure sensor 118 also could be used to determine safe placement of stents. Increasing expansion while reading perfusion intensity may result in a temporary and substantial decrease in perfusion. Thus, pressure readings from sensor 118 can be used to reduce expansion in these instances to ensure safe delivery by determining whether expansion of the stent causes a temporary restriction of blood flow.

ECG lead assembly 104 may be coupled to controller 106, and may be configured to sense an ECG signal based on electrical activity of the patient's heart sensed by one or more electrodes 120. While ECG lead assembly 104 is shown in FIG. 1 with four electrodes 120, any other suitable number of electrodes 120 may be utilized.

Controller 106 may include a processor that is generally configured to accept information from the system and system components, and process the information according to various algorithms. The processor may be a digital IC processor, analog processor or any other suitable logic or control system that carries out the control algorithms. In some implementations, controller 106 may record treatment parameters such as, e.g., sensor data, so that they may be accessed for concurrent or subsequent analysis. Controller 106 may include software that provides a user interface to components within the system. The software may enable a user (e.g., clinician) to configure, monitor, and control operation of catheter 102, ECG lead assembly 104, and control circuitry and pump components within fluid delivery device 108. As described in further detail below, the software may be configured to process a signal indicative of blood flow within a gastrointestinal tract to calculate an area indicative of a blood flow rate within the gastrointestinal tract.

Fluid delivery device 108 may include a pump, and may be configured to deliver fluid to and convey fluid from expandable member 114 to inflate and deflate expandable member 114. Fluid delivery device 108 may be controlled by controller 106, or another suitable controller. The pump may be any suitable pump, such as, e.g., a peristaltic pump, piston pump, motorized pump, infusion pump, or the like. Fluid delivery device 108 may be powered by electrical power, mechanical power, chemical power, or another suitable mechanism. Fluid delivery device 108 may include a source (e.g., a reservoir of liquid or a canister of gas) used to inflate and deflate the expandable member 114.

Referring to FIGS. 1-4, one or more sensors 116 may be disposed on an outer surface of expandable member 114. In one implementation, four sensors 116 may be circumferentially spaced about expandable member 114 about 90 degrees from one another, although other numbers of sensors and/or different spacing arrangements also are contemplated. Sensor 116 may be configured to generate a signal that can be used by controller 106 to determine blood flow, e.g., perfusion, within a gastrointestinal tract of a patient. Sensor 116 may include a first emitter 135, a second emitter 136, and a detector 137. First emitter 135 and second emitter 136 each may be configured to emit light, e.g., non-visible infrared light and/or visible light toward body tissue. For example, first emitter 135 and second emitter 136 each may include one or more light emitting diodes (LEDs). In some implementations, first emitter 135 and second emitter 136 may be configured to direct different wavelengths of light at tissue. For example, first emitter 135 may be configured to direct light of a first wavelength (e.g., red light with a wavelength from about 620 nm to about 750 nm) toward body tissue, while second emitter 136 may be configured to direct light of a second wavelength different than the first wavelength (e.g., green light from about 520 nm to about 540 nm, or at about 530 nm) toward body tissue. First emitter 135 and/or second emitter 136 may be configured to separately or simultaneously direct one or more wavelengths of light toward body tissue. For example, first emitter 135 may be configured to direct infrared light (at a wavelength from about 700 nm to about 1 mm) in addition to visible red light. Emitted light may be absorbed by the body based on the blood volume at the absorption location. Absorption occurs when elements in the blood absorb photons and diffuse light passing through the blood. Hemoglobin, for example, is an absorber of light but absorbs different light wavelengths at different rates. Backscatter is the amount of light that is reflected back to the detector and is not absorbed in the blood. Detector 137 may be a photodiode (e.g., a silicon photodiode) that is configured to receive backscattered light reflected from the body.

Each detector 137 may be longitudinally aligned (e.g., disposed at the same longitudinal location) as each other detector 137. Similarly, each first emitter 135 may be longitudinally aligned with each other first emitter 135, and each second emitter 136 may be longitudinally aligned with each other second emitter 136.

Figure 3:
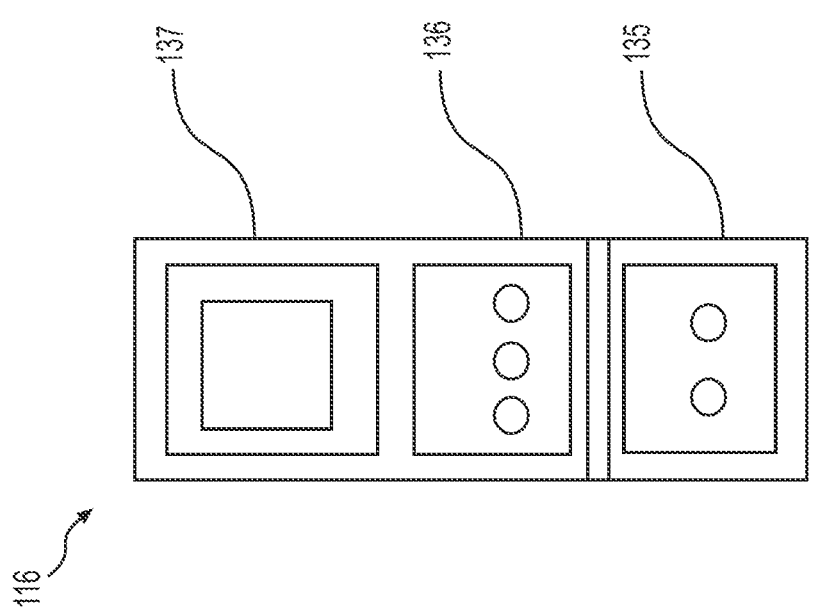
FIG. 3 is a front view of an optical sensor.

Referring to FIG. 3, detector 137 may be configured to measure reflected light that originates from an emitter (e.g., first emitter 135 and/or second emitter 136). For purposes of discussion herein, a short vector refers to reflected light detected by detector 137 that originated from an emitter on the same sensor 116 as the given detector 137. Thus, depending on the configuration of emitters on a given sensor, each detector 137 may be configured to detect light along one or more short vectors. In one implementation, where first emitter 135 is configured to emit green light, and second emitter 136 is configured to emit red light and infrared light, each detector 137 may be configured to detect light along three short vectors (green, red, infrared). Different absorption rates in blood and tissue with known correlations can be used to determine various physiological parameters (photoplethysmography), such as, e.g., oxygen saturation, heart rate, perfusion intensity, surrogate blood pressure, and tissue thickness.

Figure 4:
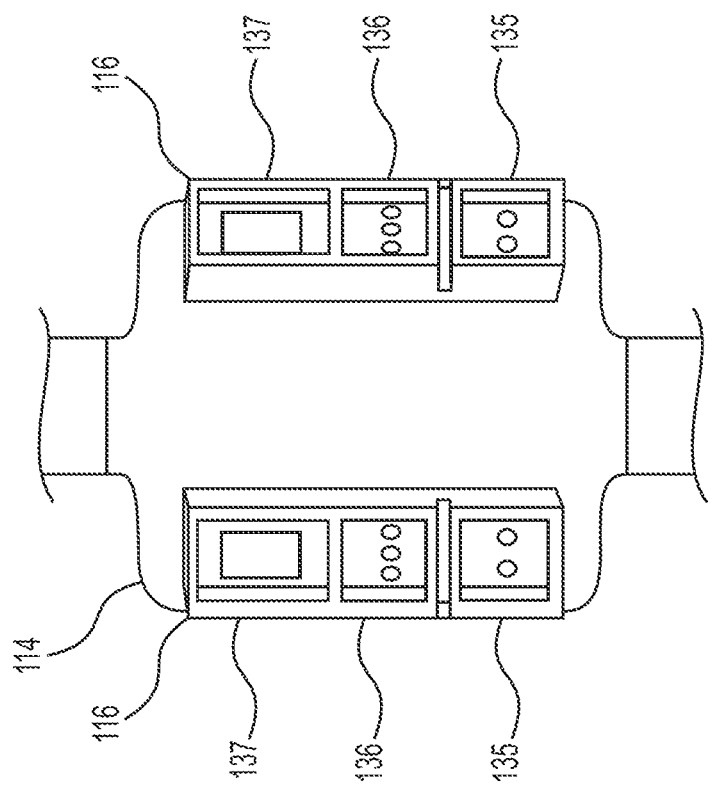
FIG. 4 is a side view of the expandable member of FIG. 2 with a plurality of optical sensors.

Referring to FIG. 4, a long vector refers to reflected light detected by detector 137 that originated from an emitter on a circumferentially adjacent emitter. Thus, when a given sensor 116 is disposed circumferentially between two other sensors 116, the detector 137 of the given sensor 116 may be configured to detect light from one or more long vectors from each of the two adjacent sensors (emitters). In the implementation where first emitter 135 is configured to emit green light, and second emitter 136 is configured to emit red light and infrared light, each detector 137 may be configured to detect light along six long vectors (three long vectors originating from each of the two circumferentially adjacent sensors 116).

In one implementation of the disclosure where four sensors 116 are disposed around the circumference of expandable member 114, system 100 may record measurements along a total of 36 vectors (12 short vectors and 24 long vectors). Each of the four sensors 116 includes three short vectors, totaling 12 short vectors. Additionally, each of the four sensors 116 includes six long vectors as set forth above, totaling 24 long vectors. Devices with only one optical sensor may have a single vector, which would not enable mapping of the blood vessels around the lumen, the determination of tissue thickness, or the data necessary to size a stent during deployment.

Figure 5:
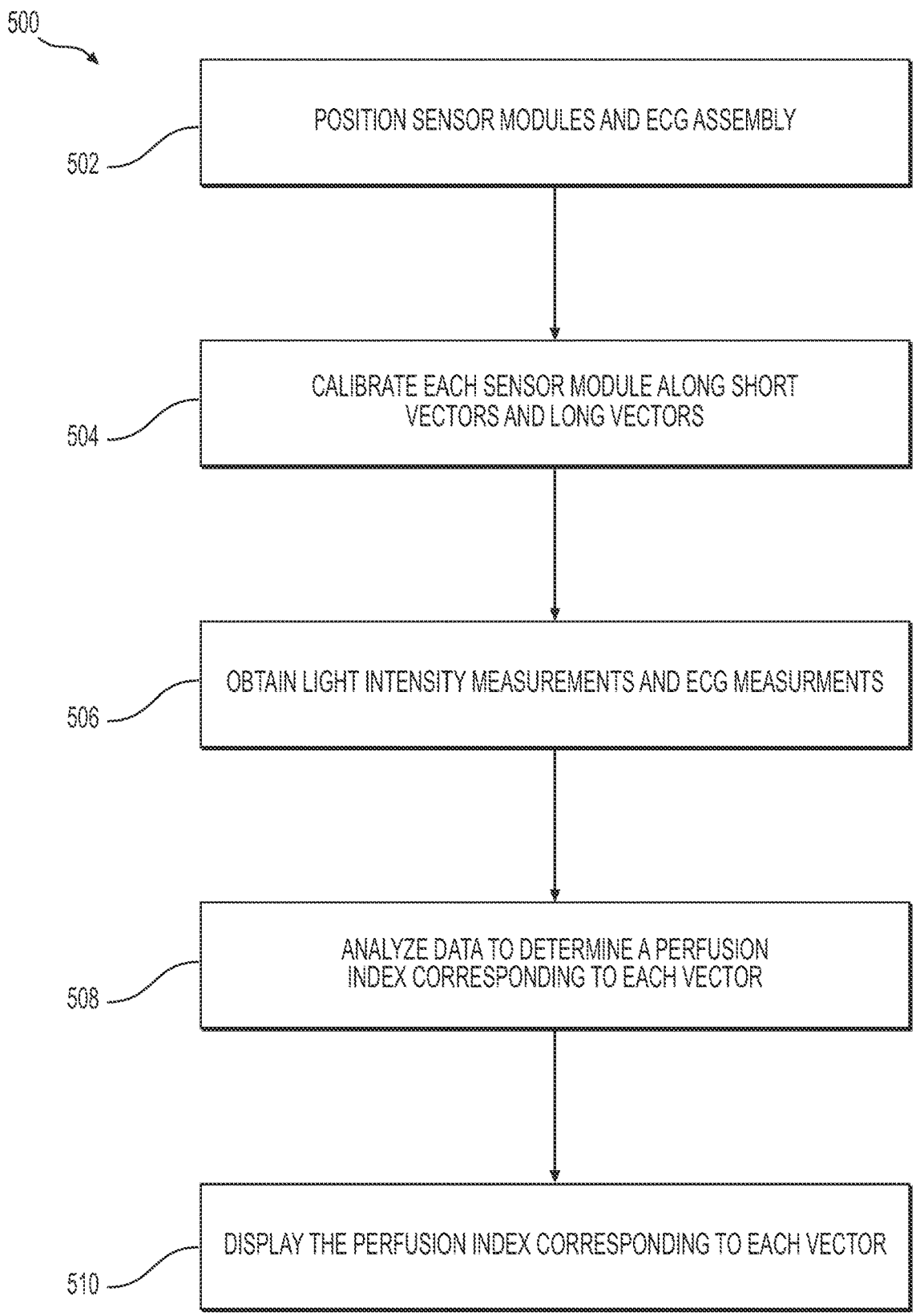
FIG. 5 is a flowchart of a method, according to an implementation of the disclosure.

Referring now to FIG. 5, an exemplary method 500 is shown. Method 500 may begin at step 502, where sensors 116 and ECG assembly 104 may be deployed. For example, catheter 102 may be orally inserted into a patient through the nose or mouth and into the gastrointestinal tract through the esophagus and stomach. Using fluoroscopic, ultrasonic, anatomic, or CT guidance, an endoscope (or expandable member 114 alone) may be positioned at a location (region of interest) within the gastrointestinal tract such as the duodenum. The region of interest then may be visualized using an imaging device (e.g., an endoscopic camera), and expandable member 114 may be extended to the region of interest via a working port of the endoscope. Once expandable member 114 is positioned at the location (region of interest), it may be expanded via fluid from fluid delivery device 108. Before, during, or after insertion of catheter 102 into the body, electrodes 120 of ECG lead assembly 104 may be placed on a suitable site of a patient, such as the patient's chest, to monitor electrical activity of the heart. With expandable member 114 and sensors 116 in position, all other light emitting sources in the body lumen, such as, e.g., a guiding light of an endoscope, may be turned off to avoid interfering with measurements detected by sensor 116.

Method 500 may proceed to step 504, where the system 100 may calibrate sensors 116. At step 504, the required gains for detectors 137 and drive currents for the emitters 135 and 136 may be determined. In one implementation, calibration may be accomplished sequentially for each sensor 116. Calibration for the short vector reflections of each wavelength (e.g., red, infrared, and green) may take place for each sensor 116. Each of the sensors 116 will be calibrated for each of its short vectors, and the values for the detector gain and current setting for the emitters 135 and 136 may be stored. Then, each sensor 116 may be calibrated for its associated long vectors for each wavelength (e.g., red, infrared, and green) for each circumferentially adjacent sensor.

The primary purpose of the calibration is to optimize the signal to noise ratio received by detector 137. The secondary purpose is to obtain the values of the gain and current settings for each vector, which are then used as scoring factors in mapping out the tissue perfusion around the body lumen.

After calibration, method 500 may proceed to step 506, where light intensity measurements over time may be made continuously and sequentially for each of the 36 vectors. In some implementations, each detector 137 may be configured to perform more than one measurement at a given time (e.g., pulse, blood oxygen, surrogate blood pressure, mean arterial pressure, perfusion intensity, tissue thickness). Controller 106 may associate a time stamp to each measurement performed, or may otherwise associate the time of day with each waveform collected by each detector 137. ECG lead assembly 104 may collect ECG data at all times that any detector 137 is collecting optical data.

After collecting data at step 506, method 500 may proceed to step 508, where the collected data may be analysed to generate a perfusion index corresponding to each vector at one or more wavelengths. Perfusion index may be the ratio of the pulsatile blood flow to the non-pulsatile static blood flow. Perfusion index is an indication of pulse strength at the measurement site, and may be indicative of tissue inflammation around the measurement site. The perfusion index may be calculated based on a determined perfusion intensity, which is a measure of blood velocity and its peak amplitude. The perfusion intensity may be determined using a pulse transit time (PTT) and a height of an associated P wave. PTT is the time it takes a pulse pressure (PP) waveform to propagate through a length of an arterial tree. The pulse pressure waveform results from the ejection of blood from the left ventricle and moves with a velocity much greater than the forward movement of the blood itself. The P wave represents atrial depolarization, which may result in atrial contraction.

The data collected for each vector will be weighed against the calibration values (gain and current), and used to create a perfusion intensity map. Higher gain settings and currents may be flagged as suspected low perfusion regions when looking at P wave heights. The perfusion intensity map then may be manipulated to create a perfusion index map.

Figure 6A:
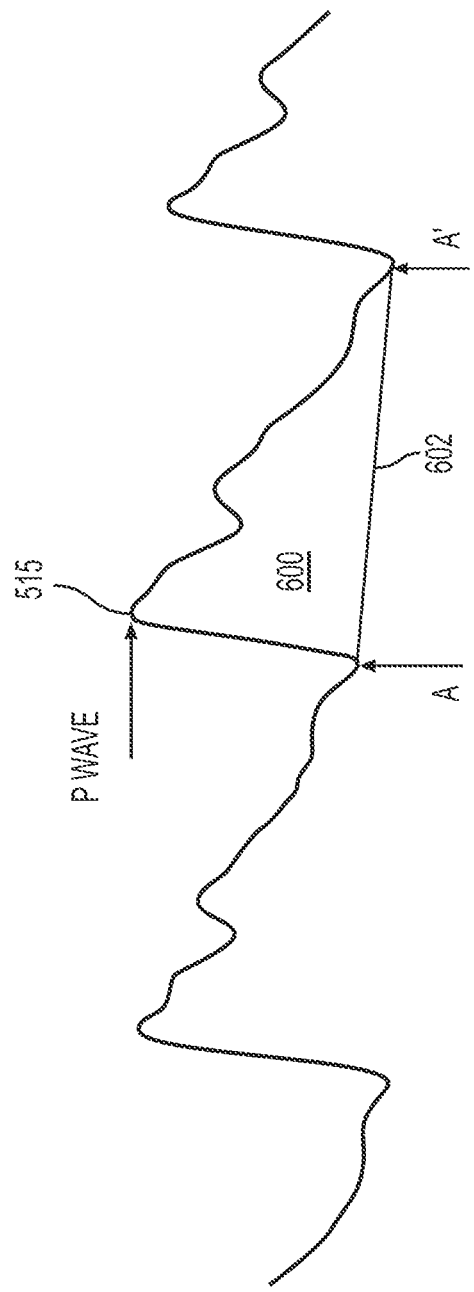
FIG. 6A is illustration of an electrocardiogram measured by the system of FIG. 1.
Figure 6B:
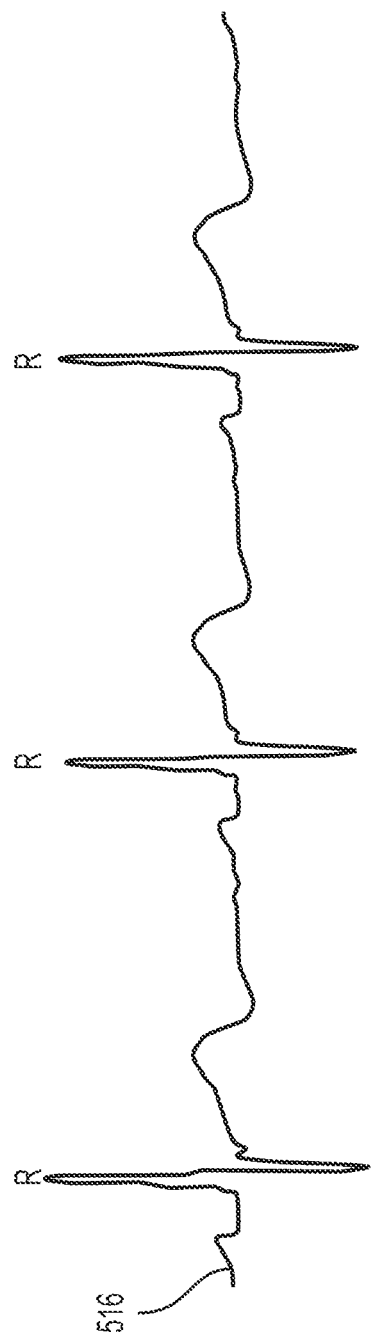
FIG. 6B is an illustration of a photoplethysmogram measured by the system of FIG. 1.

The measured data from sensors 116 may be filtered using a suitable filter, such as a High-Pass Finite Impulse Response (FIR) filter, to remove noise in the data, such as noise caused by distortion created by mechanical ventilation or intestinal peristalsis. For each vector, a PPG signal 515 (FIG. 6A) and an ECG signal 516 (FIG. 6B) may synchronized relative to time at a suitable frequency, e.g., 100 Hz. This synchronization is illustrated in FIGS. 6A and 6B, which shows the PPG signal 515 over time (FIG. 6A) for a given vector, and the corresponding ECG signal 516 obtained at the same time.

Figure 7:
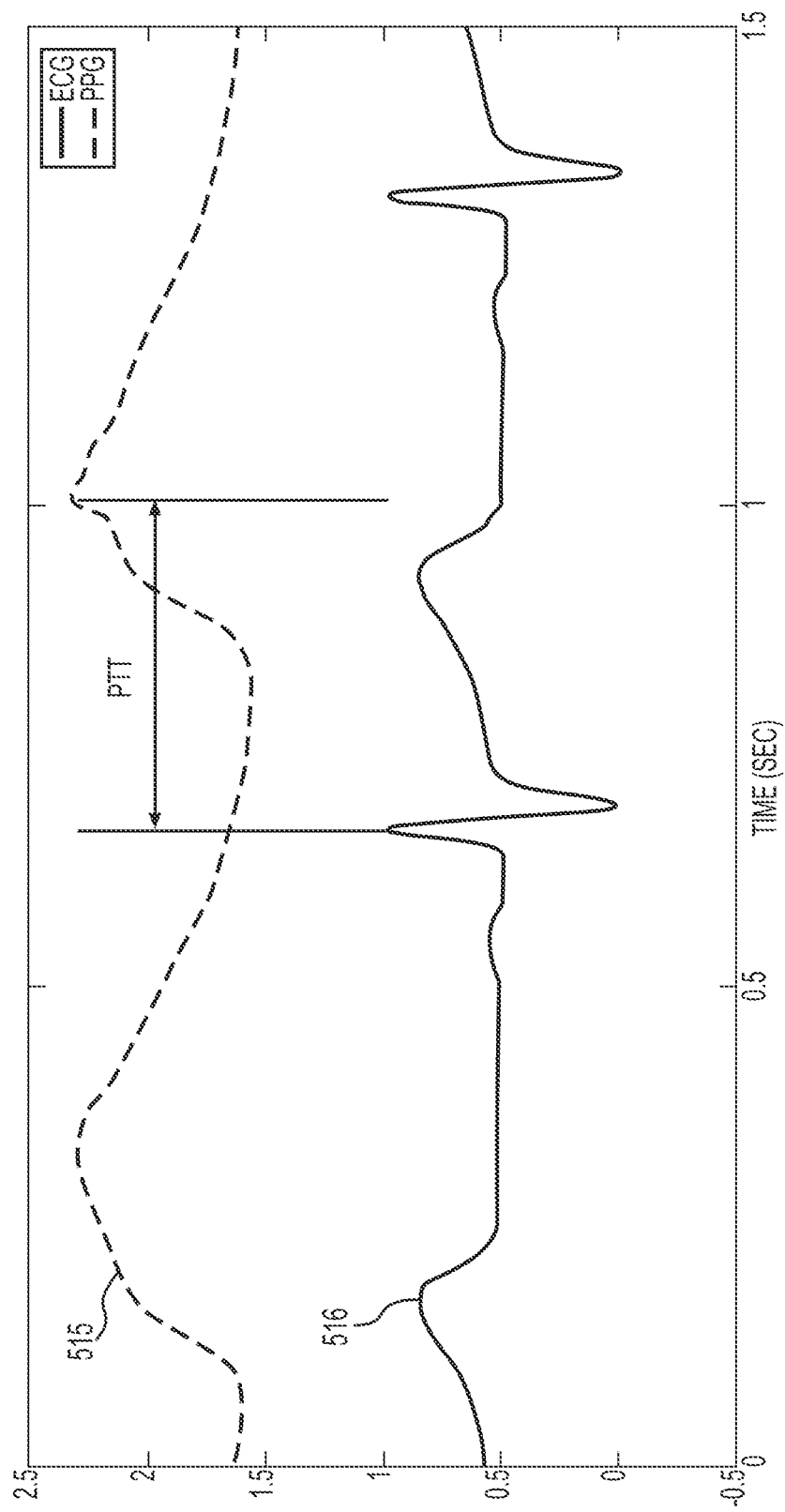
FIG. 7 is a depiction of the electrocardiogram of FIG. 6A and the photoplethysmogram of FIG. 6B on common axes.

The data based on the ECG signal 516 is used to determine an R wave signal. Controller 106 may determine the R wave signal using a derivative based algorithm. Referring to FIG. 6B, a graph is illustrated depicting ECG signal 516 having determined R waves marked with the letter R. R waves may be used as a trigger to identify PTT. The PTT may be calculated as the time of flight from the R wave of the ECG signal 516 to an associated P wave of PPG signal 515 (see FIGS. 6A, 6B, and 7).

Referring back to FIG. 6A, an area 600 under PPG signal 515 may be calculated. This area may represent the volume of pulse as a part of the intensity calculation. The PPG signal 515 is searched between two consecutive R waves, which are used to determine a time window in which to search for a minimum value (shown as "A" in FIG. 6A) of a segment of the PPG signal 515. The minimum point A on the PPG signal 515 within the time window after the R wave is used as the starting point of a PPG segment. The ending point of the PPG segment is where the next minimum point of the PPG signal is detected (shown as A' in FIG. 6A), which is also a starting point for the next PPG segment. To calculate AC area 600, a boundary line 602 is drawn between minimum points A and A' on the PPG curve. AC area 600 may be the area below PPG signal 515, above boundary line 602, and between minimum points A and A'.

Once area 600 is determined for each vector, a perfusion intensity $I_{Perf}$ may be calculated by dividing the AC area 600 (pulse area) for each vector by the PTT of the same vector. To create the perfusion index, perfusion intensity $I_{Perf}$ may be normalized for all 36 vectors as each may have different gain and current settings. Additionally, it is expected that the 24 long vectors will require higher current and gain settings than the short vectors. Short vector perfusion intensities may be calculated and compared separately from perfusion intensities of the longer vectors. A short vector perfusion index (SV_Index$_n$) for each of the 12 short vectors may be calculated using the following equation:

$$SV\_Index_n = \frac{I_{Perf_n}}{GAIN_n \times I_{LED_n}}$$

$I_{LED_n}$ represents a current associated with a respective LED. A normalization (k) will be made between short and long vectors to create a normalized scoring index. Longer vectors require more current to get a reading that is at an acceptable level above a signal to noise ratio (SNR), and possibly require more gain. k may act as a scaling factor to compensate the larger gain and current settings. Determination of k may require empirical testing in some examples, and may include a balance between the short vector I_Perfn settings with the long vector I_Perf_n settings, for example, where SV_I_PERF=LV_I_PERF. If the resulting intensity measurements are kept the same, k may be the ratio of gain and current setting of long vectors over that of the short vectors.

The following equation may be used to calculate a long vector index (LV_Index$_m$), where k is used to scale the result so it is normalized with the short vectors.

$$\text{LV\_Index}_m = \frac{I_{Perf_m}}{GAIN_m \times I_{LED_m}} k$$

Figure 8:
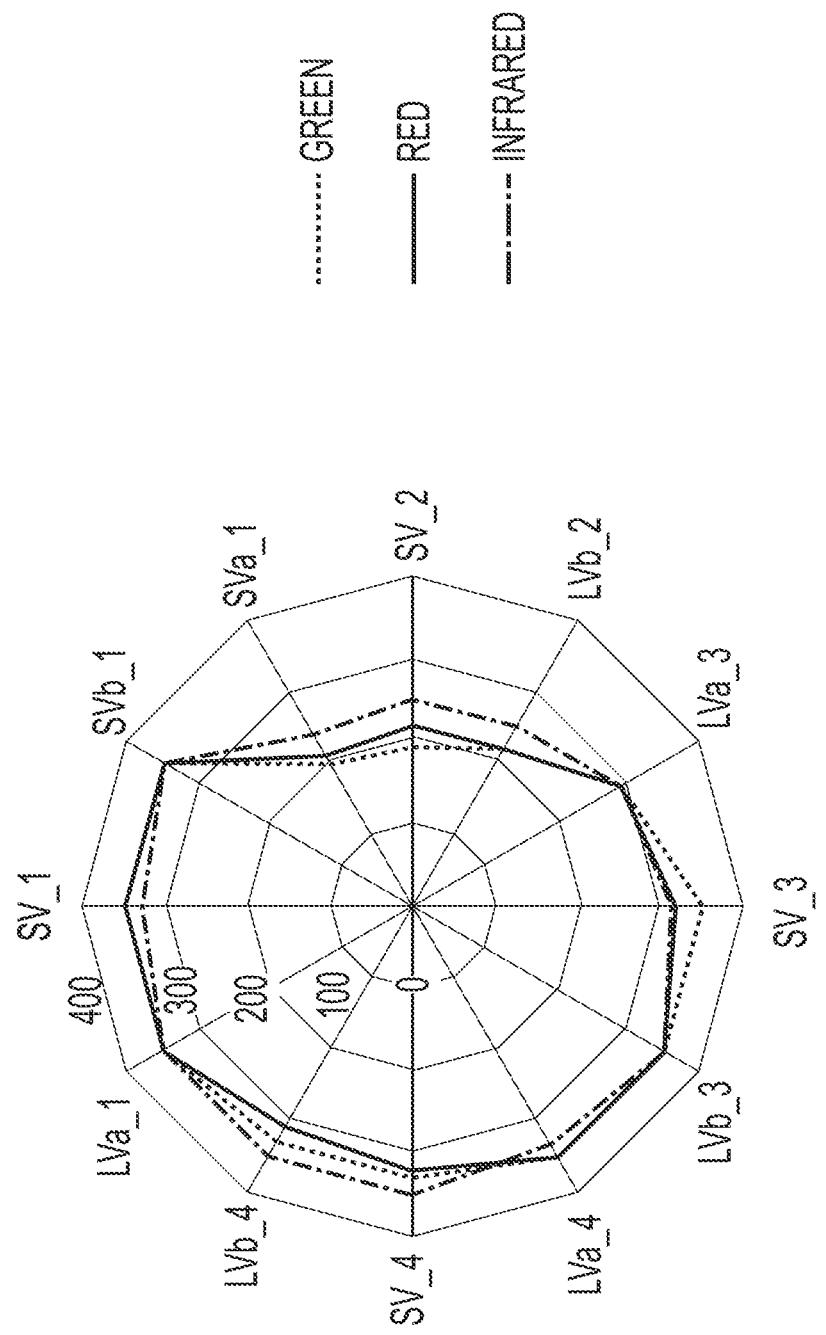
FIG. 8 is an illustration of a perfusion index created using optical data measured by the system of FIG. 1.

The indexing score values may be represented as a radial map (see FIG. 8), which when viewed (method step 510), gives a visual representation of perfusion index around the body lumen where the measurements were taken with sensors 116. For illustration, a low perfusion is shown around the SV_2 portion and adjacent long vectors.

Figure 9:
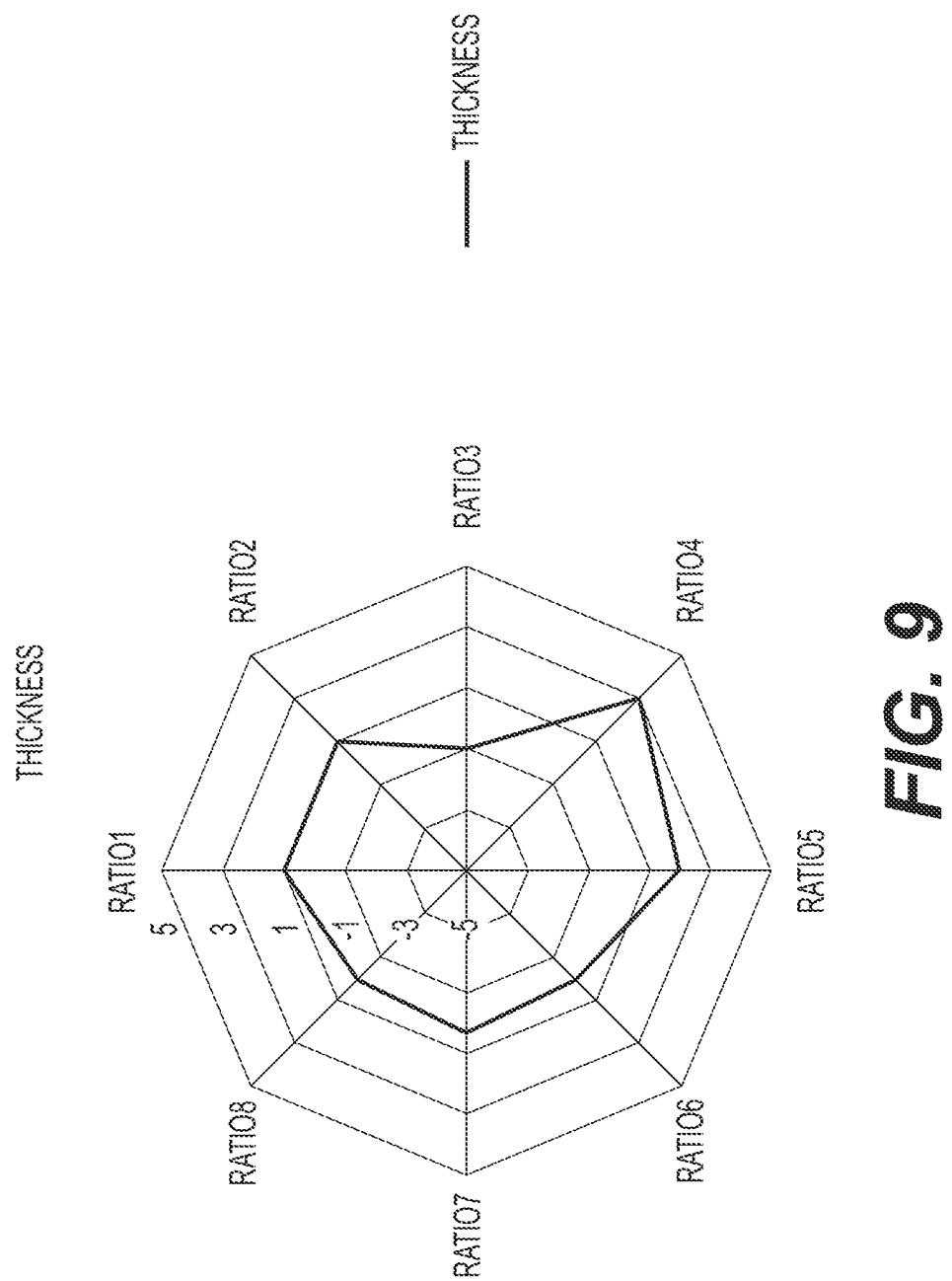
FIG. 9 is an illustration of tissue thickness created using optical data measured by the system of FIG. 1.

For two wavelengths (e.g., green and red wavelengths), a variation of the Green's function of a diffusion into a substance can be used with a slope-ratio method to determine tissue wall thickness. The spectral ratio of slopes shown in FIG. 9 represent the difference between short vector perfusion to long vector perfusion of the green wavelength over the difference of the short vector perfusion to long vector perfusion of the red wavelength.

$$\text{Ratio} = \frac{\text{SV\_Index}_{green} - LV_{Index\,green}}{\text{SV\_Index}_{red} - LV\_\text{Index}_{red}}$$

This may be evaluated for each position around the sensor array. This ratio may approximate tissue thickness surrounding a body lumen and sensor array. In the example having four optical modules around a circumference of an expandable member, there are two long vectors for each short vector, and thus eight regional ratios. In some examples, slope tomography may be used to determine tissue wall thickness.

While the slopes used in some examples herein utilize multiple wavelengths of visible light (e.g., green and red), it other examples, combinations of visible and non-visible light may be used to determine tissue wall thickness, such as, e.g., green and IR, or red and IR.

After step 510, method 500 may return to step 502 for repositioning of expandable member 114 for additional measurements at different locations in the body.

Figure 10:
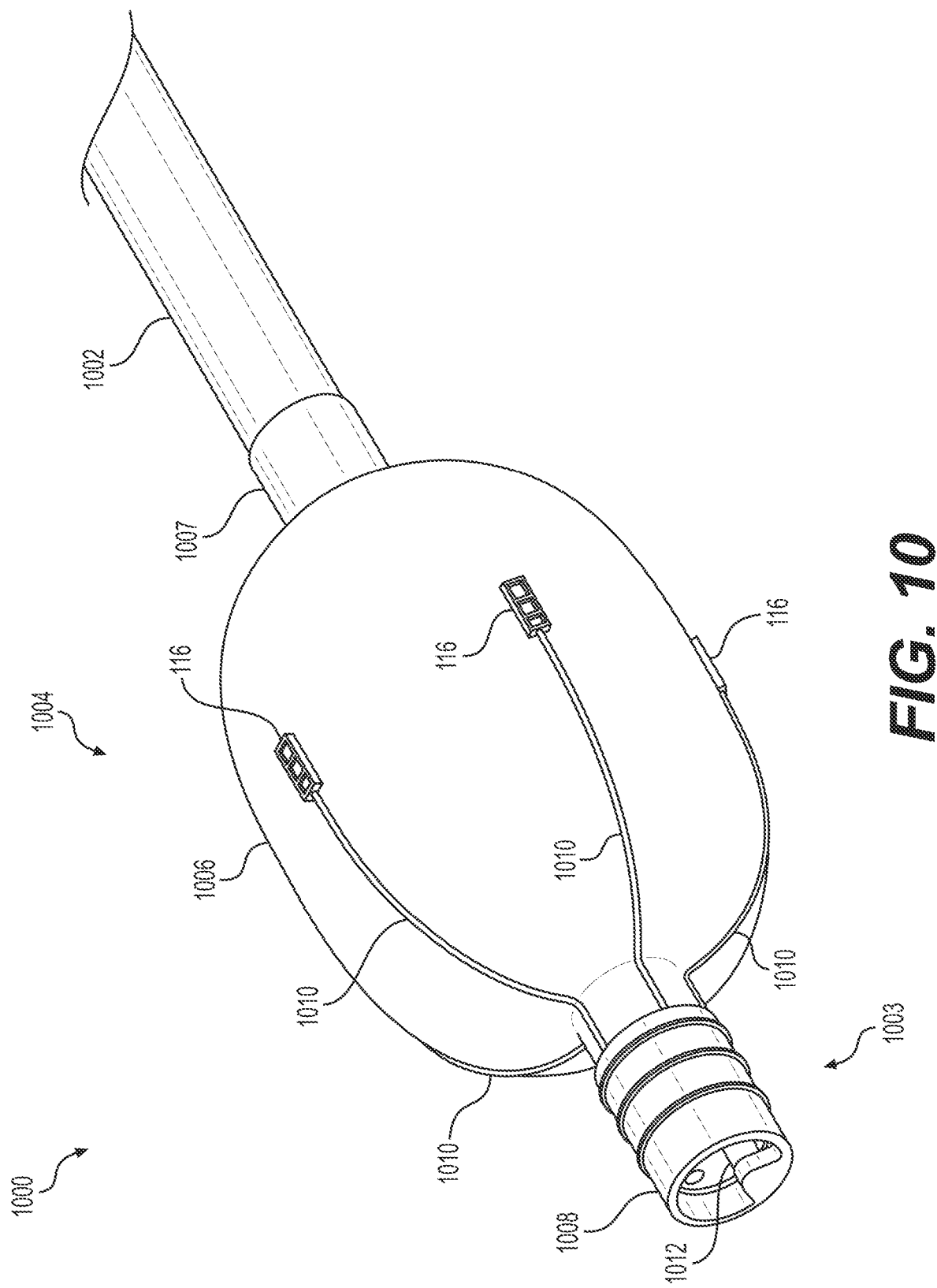
FIG. 10 is a perspective view of an expandable member and a plurality of sensors, according to another implementation of the present disclosure.

More complicated cases of Crohn's Disease, where a stricture may prevent the advancement of a scope/sensor array, may require extra steps of deploying a dilating device to open a passageway, and re-deploying the sensor array. FIGS. 10-13 show various "over-the-scope" devices with sensors 116 that can be used in these more complicated cases. In particular, FIG. 10 shows a system 1000 including an endoscopic device 1002 extending from a proximal end (not shown) to a distal end 1003. Endoscopic device 1002 may be any suitable endoscopic member, such as, e.g., an endoscope, a ureteroscope, a nephroscope, a colonoscope, a hysteroscope, a uteroscope, a bronchoscope, a cystoscope, a sheath, or a catheter. Endoscopic device 1002 may include one or more additional lumens configured for the passage of a variety of tools and devices, including, but not limited to, imaging devices and tools for irrigation, vacuum suctioning, biopsies, and drug delivery. Endoscopic device 1002 also may include an imaging device, e.g., a camera, at distal end 1003.

System 1000 may include a sensor assembly 1004 having an expandable member 1006 disposed between a proximal cuff 1007 and a distal cuff 1008. Proximal cuff 1007 and distal cuff 1008 each may extend around an exterior surface of endoscopic device 1002, and may be secured to endoscopic device 1002 by an interference fit or other suitable mechanism. Additionally, in system 1000, a distalmost end of distal cuff 1008 may be positioned distal to a distalmost end of endoscopic device 1002.

One or more sensors 116 may be disposed on an outer surface of expandable member 1006 in a substantially similar manner as described above with respect to sensors 116 and expandable member 114. In system 1000, each sensor 116 may be coupled to a control member (e.g., control wire) 1010 that is extended through a working channel of endoscopic device 1002 and connected at its proximal end to controller 106 (shown in FIG. 1). For example, control members 1010 may be bundled into a sheath 1012, and sheath 1012 may be extended through the working channel of endoscopic device 1002. Distal portions of each control member 1010 also may be positioned on an exterior surface of expandable member 1006 and ultimately coupled with a given sensor 116. Similar to expandable member 114, expandable member 1006 may be a compliant or semi-compliant balloon configured to inflate and deflate via a fluid conveyed by fluid delivery device 108 (shown only in FIG. 1). Sheath 1012 also may include a lumen coupled to fluid delivery device 108 to convey fluid to and from expandable member 1006 for inflation and deflation. Alternatively, expandable member 1006 may be coupled to fluid delivery device 108 by another mechanism.

Figure 11:
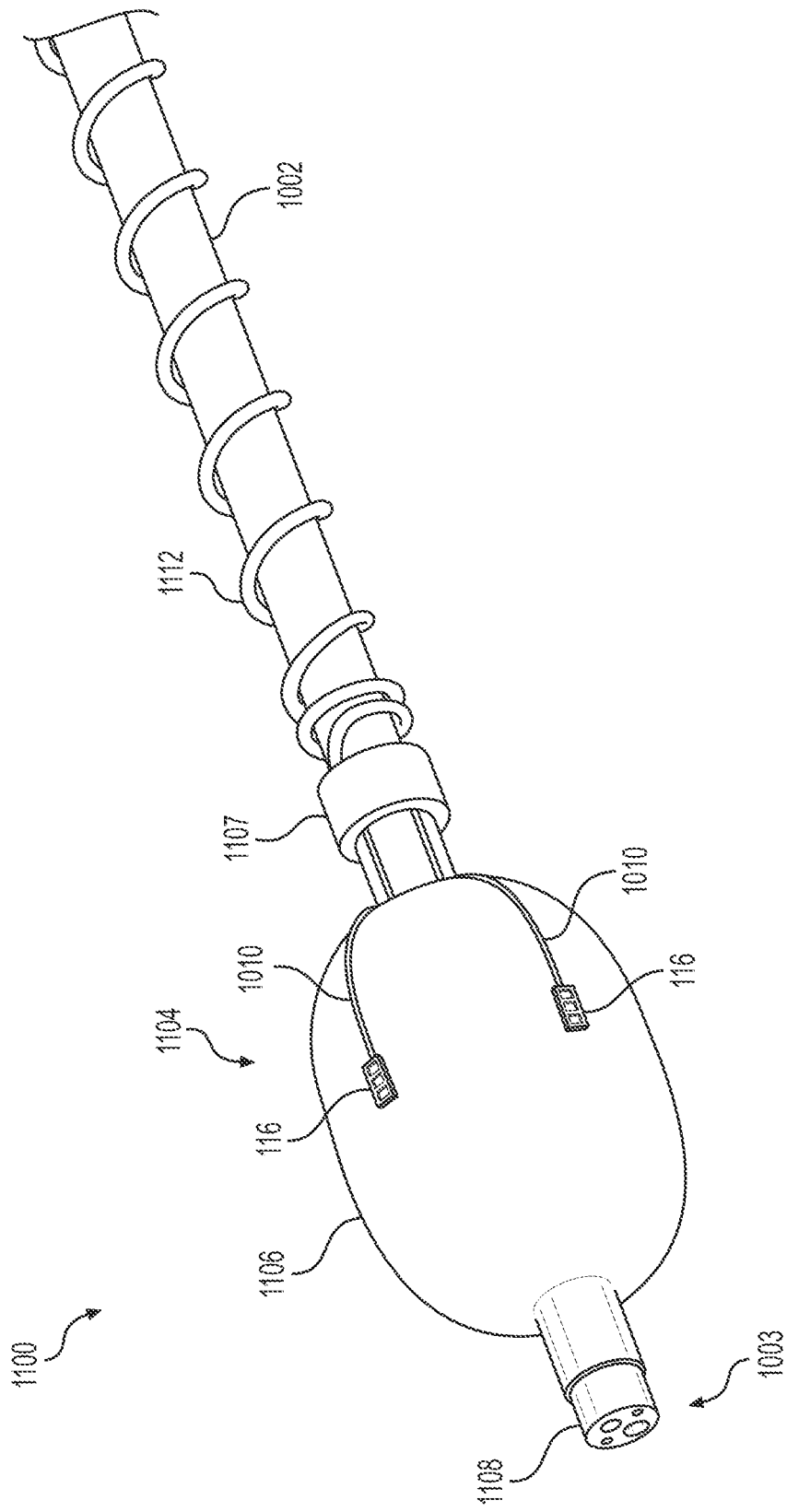
FIG. 11 is a perspective view of an expandable member and a plurality of sensors, according to yet another implementation of the present disclosure.

A system 1100 is shown in FIG. 11, including a sensor assembly 1104 positioned over endoscopic device 1002 (e.g., the same endoscopic device described with reference to FIG. 10). Sensor assembly 1104 may include an expandable member 1106 disposed between a proximal cuff 1107 and a distal cuff 1108. Proximal cuff 1107 and distal cuff 1108 each may extend around an exterior surface of endoscopic device 1002, and may be secured to endoscopic device 1002 by an interference fit or other suitable mechanism. Additionally, a distalmost end of distal cuff 1108 may be positioned proximal to a distalmost end of endoscopic device 1002.

One or more sensors 116 may be disposed on an outer surface of expandable member 1106. The arrangement of the sensors 116 on expandable member 1106 may be similar to the arrangement of sensors 116 on expandable member 1006 set forth above, except that control members 1010 may be positioned entirely external to endoscopic device 1002. For example, control members 1010 may be bundled into a sheath 1112, and sheath 1112 may extend along the exterior of endoscopic device 1002. Similar to sheath 1012, sheath 1112 also may include a lumen coupled to fluid delivery device 108 (shown in FIG. 1) to convey fluid to and from expandable member 1106 for inflation and deflation.

Figure 12:
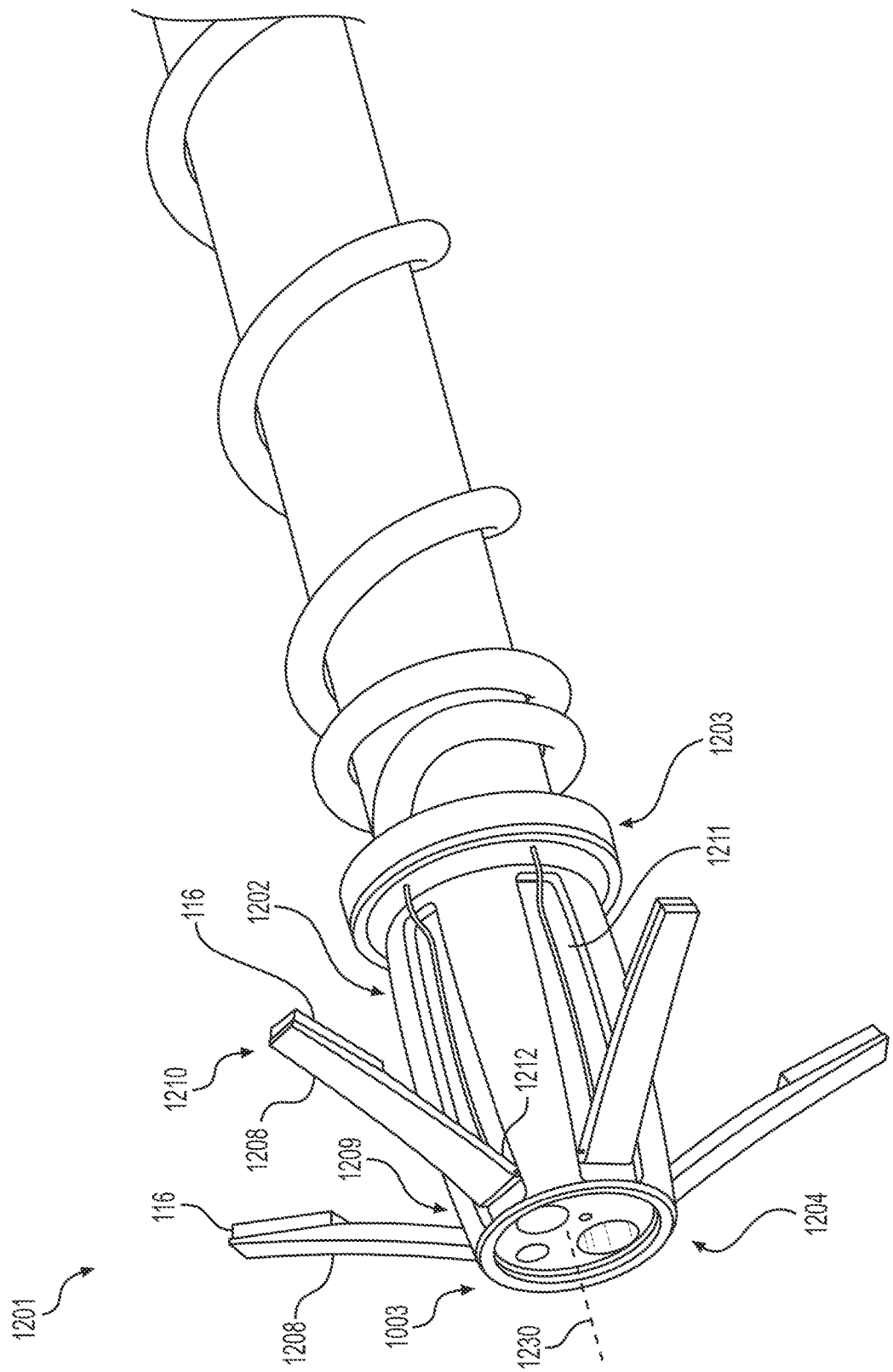
FIGS. 12 and 13 show un-deployed and deployed configurations, respectively, of an expandable member and a plurality of sensors, according to yet another implementation of the present disclosure.
Figure 13:
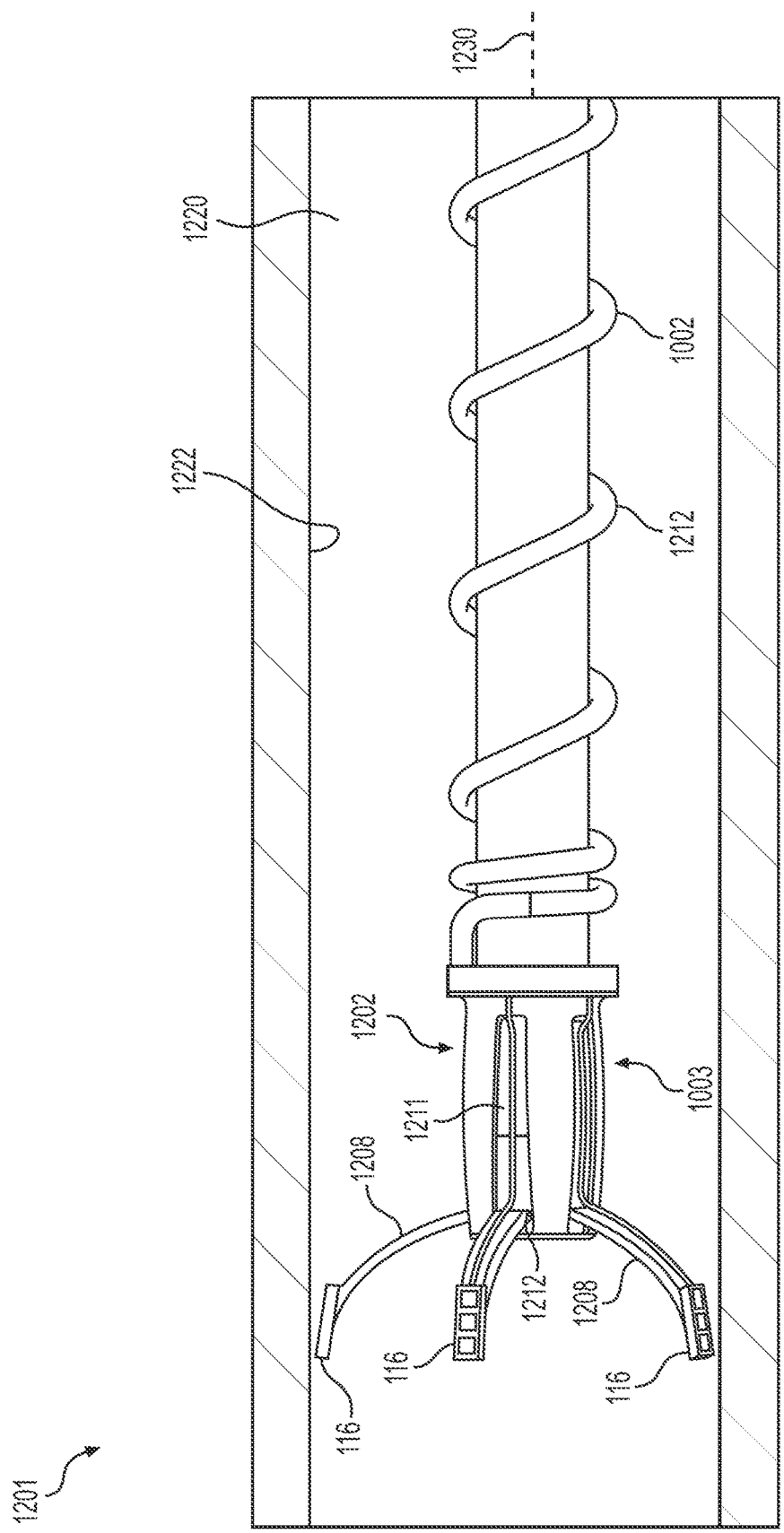

A sensor assembly 1201 is shown in FIGS. 12 and 13 in un-deployed and deployed configurations, respectively. Sensor assembly 1201 may be coupled to distal end 1003 of endoscopic device 1002, and may be configured to position one or more sensors 116 in contact with an inner surface 1222 of a body lumen 1220 (referring to FIG. 13). Sensor assembly 1201 may include a cuff 1202 having a proximal end 1203 and a distal end 1204. Cuff 1202 may slide onto distal end 1003 of endoscopic device 1002. Cuff 1202 may include one or more flexible arms 1208 that are circumferentially spaced apart from one another. Each arm 1208 may include a set curvature. For example, each arm 1208 may have a preset shape in a deployed configuration. As shown in FIGS. 12 and 13, each arm 1208 may include a concave curvature when viewed from a perspective distal to the arm 1208, and may include a convex curvature when viewed from a perspective proximal to the arm 1208. Arms 1208 may be biased into either the un-deployed or deployed configuration.

Each of the one or more arms 1208 may include a mounted end 1209 and a free end 1210. Each of the one or more arms 1208 may be at least partially disposed in a corresponding recess 1211 in cuff 1202. Thus, each recess 1211 may be circumferentially offset from each other recess 1211 of cuff 1202. Mounted end 1209 of each arm 1208 may form a hinge 1212 with cuff 1202. Arms 1208 may move from a first, un-deployed position, where free end 1210 is disposed proximally of mounted end 1209, to a second, deployed position, where free end 1210 is disposed distally of mounted end 1209. Arms 1208 may be moved between the first and second positions by manipulating endoscopic device 1002 to cause free ends 1210 to engage with tissue. For example, distal movement of endoscopic device 1002 may cause tissue of a body lumen to push proximally against free ends 1210, moving arms 1208 into the configuration shown in FIG. 12. On the contrary, proximal movement of endoscopic device 1002 causes tissue of the body lumen to push distally against free ends 1210, moving arms 1208 into the configuration shown in FIG. 13. Thus, arms 1208 may be moved between un-deployed and deployed positions by only passive mechanisms without any powered and/or automated components. Alternatively, arms 1208 may be actively moved between the un-deployed and deployed configurations by an active mechanism, such as, e.g., a combination of motors, gears, and actuators. For example, a user may activate an actuator that causes a combination of motors and gears to move arms 1208 between the un-deployed and deployed positions. Furthermore, in one embodiment, each arm 1208 may lie flat/flush within a corresponding recess 1211, and an actuator may release each arm 1208 when arms 1208 are positioned at a desired tissue site.

A sensor 116 may be coupled to free end 1210 of each arm 1208. When arms 1208 are in the first, un-deployed position shown in FIG. 12, the optical components of sensors 116 may face radially inward toward a central longitudinal axis 1230 of sensor assembly 1201, and may not be operable. In the second, deployed position shown in FIG. 13, the optical components of sensors 116 may face radially outward away from central longitudinal axis 1230 and toward surface tissue 1222. Similar to the device shown in FIG. 11, control members 1010 may be positioned entirely external to endoscopic device 1002. For example, control members 1010 may be bundled into a sheath 1212, and sheath 1212 may extend along the exterior of endoscopic device 1002.

The systems shown in FIGS. 10 and 11 may be configured to operate in a similar manner as set forth in step 502 of method 500 (FIG. 5). For example, the region of interest may be observed using an imaging device (e.g., endoscopic camera). Then, instead of deploying catheter 102 to the region of interest, distal end 1003 of endoscopic device 1002 may be advanced to the region of interest, where a respective expandable member (1006 or 1106) is expanded to position sensors 116 in contact with tissue. The system shown in FIGS. 12 and 13 also may operate in a similar manner. For example, after visualization of the region of interest using the system of FIGS. 12 and 13, distal end 1003 of endoscopic device 1002 may be extended distally of the region of interest, and then pulled proximally to the region of interest to cause arms 1208 to move from the first, un-deployed configuration to the second, deployed configuration.

The systems shown in FIGS. 10-13 also may stabilize the endoscopic devices on which they are deployed, and centralize the field of view within the lumen being observed. These devices also may be used to stretch out folds within the observed lumen to improve visibility in areas that are difficult to see (e.g., around or within folds in the colon and/or intestinal walls). These effects may improve diagnostic outcomes. Yet another advantage of at least certain embodiments of these devices may be to free up the working port of the endoscopic device, enabling an operator to deploy other medical devices (for, e.g., irrigation, hemostasis stabilization, suturing, tissue sampling, or the like). Devices and methods of the present disclosure may help quantify the severity of tissue damage or healing following treatment, improving diagnostic outcomes by making them less speculative. This may be particularly relevant for inflammatory bowel diseases and ulcerative colitis. Furthermore, at least certain embodiments of devices and methods of the disclosure help improve diagnostic techniques by enabling the measurement of perfusion and thickness in regions of interest. These measurements also help enable physicians to follow the progression of treatment. Furthermore, it is contemplated that any of the inflatable members (e.g., balloons) described herein may be shaped such that, in one or more inflated configurations (including a fully inflated configuration), the outer surface of the balloon contacts less than an entirety of a body lumen (e.g., 270 degrees or less, 180 degrees or less, 90 degrees or less around the lumen).

Figure 14:
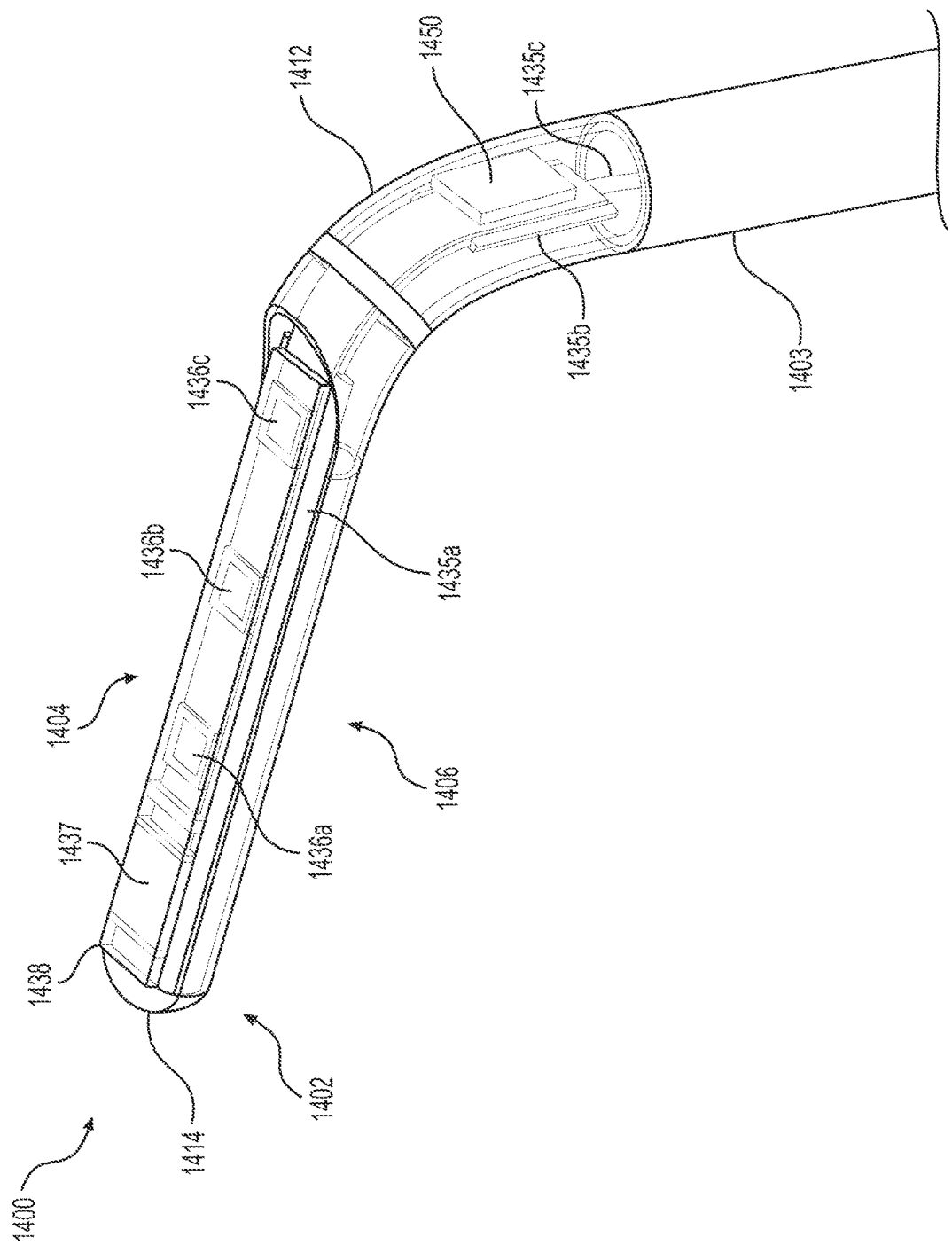
FIG. 14 is a perspective view of an optical sensor according to another implementation of the present disclosure.
Figure 15:
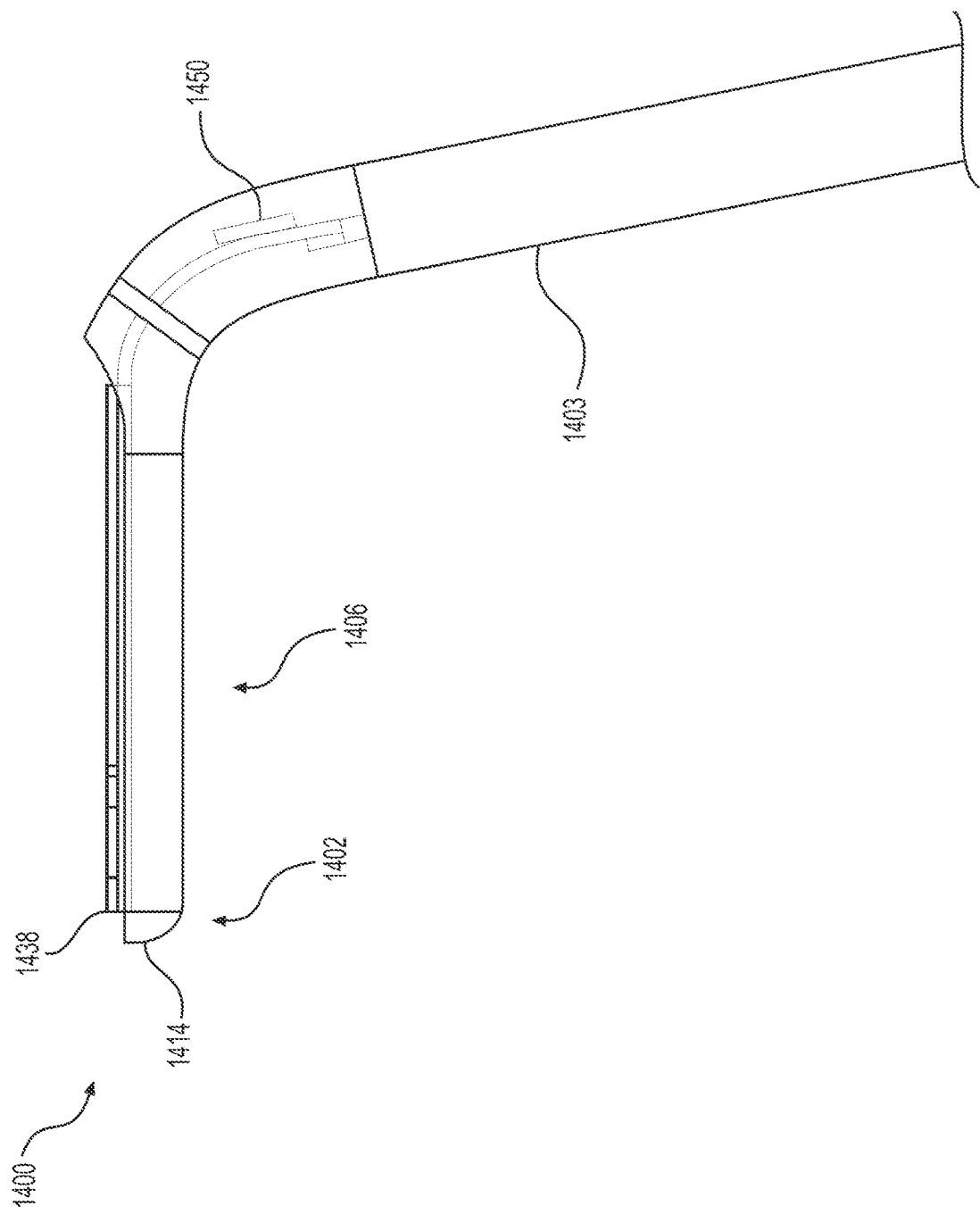
FIG. 15 is a side view of the optical sensor of FIG. 14.
Figure 16:
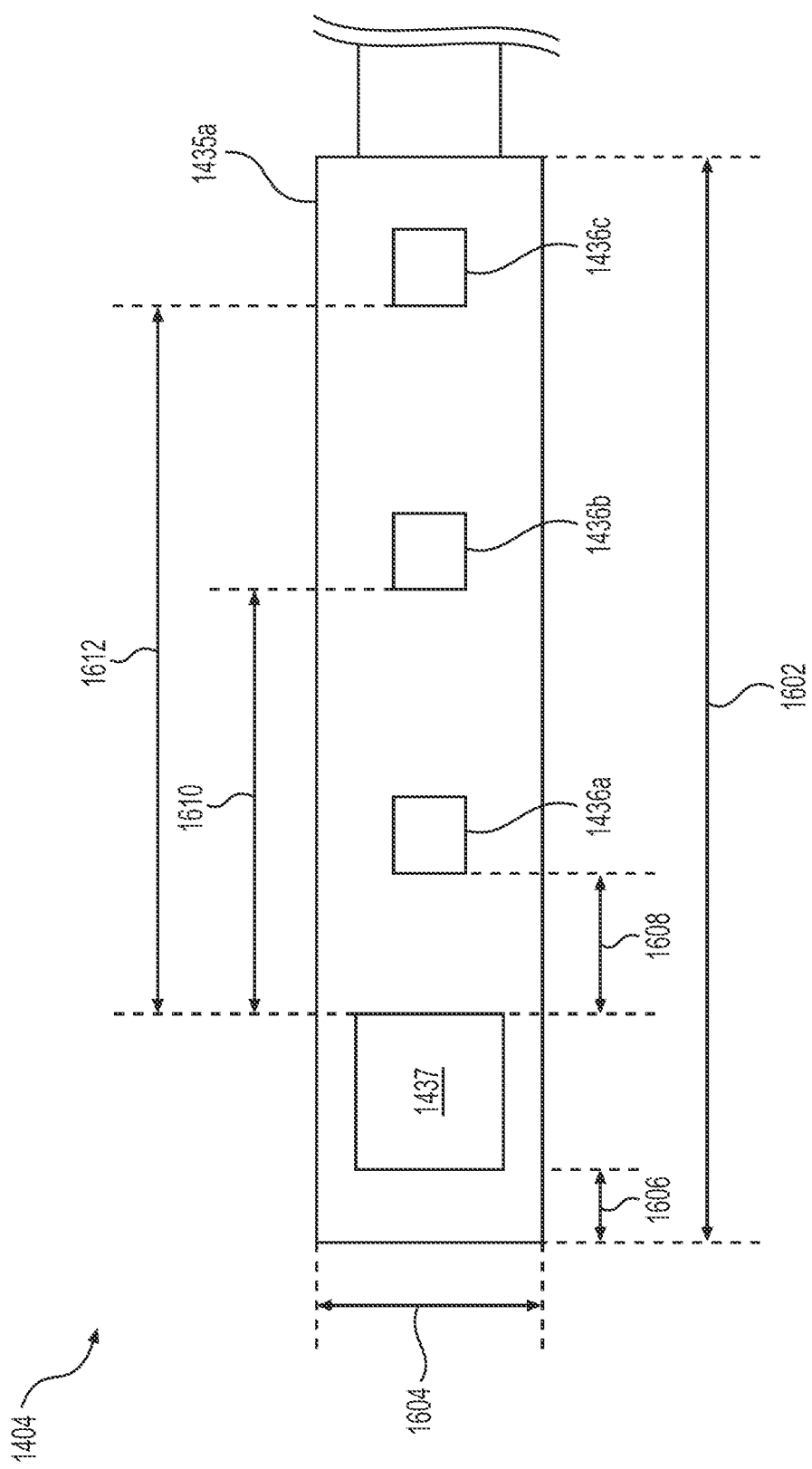
FIG. 16 is a top view of a portion of the optical sensor of FIG. 14.

A medical device 1400 is shown in FIGS. 14-16. Medical device 1400 extends from a proximal end (not shown) toward a distal end 1402. Medical device 1400 may have a relatively slim profile, and may be used to measure tissue thickness in areas of the body that are not accessible by larger devices. Medical device 1400 may include a diagnostic catheter with at least a two-way steering mechanism. Such a catheter could be made for deployment in a 3.7 mm working port of an endoscope so that it can be visually placed at the region of interest, allowing for tangential tissue measurements.

Medical device 1400 includes a catheter 1403 and an optical sensor 1404 disposed at or adjacent to distal end 1402. Catheter 1403 may be a hollow catheter having an open distal portion 1406 in which optical sensor 1404 rests. A majority of catheter 1403 may have a circular cross-section. However, open distal portion 1406 may have a different cross-section, such as, e.g., a half-moon shaped cross-section or another suitable design that enables components of optical sensor 1404 to be placed flush against tissue. Thus, optical components of optical sensor 1404 may face radially outward from a side-facing surface of catheter 1403 (a surface that faces a direction perpendicular to a longitudinal axis of catheter 1403). Open distal portion 1406 may include a distal and side facing opening of catheter 1403. The side-facing portion of the opening may extend distally of the distal facing opening.

Catheter 1403 also may include an articulating joint 1412. Control cables (not shown) may be connected to a set of control knobs at the proximal end of medical device 1400, and to articulating joint 1412 to control articulation of articulating joint 1412. By manipulating the control knobs, an operator may be able to actuate, or bend, articulating joint 1412 during insertion and direct it to a region of interest. Catheter 1403 also may include an atraumatic tip 1414. For example, tip 1414 may include a soft or flexible material to allow catheter 1403 to navigate and traverse the tortuous pathways of a body in a generally atraumatic manner.

A substrate 1435*a* may be disposed at open distal portion 1406 of catheter 1403. Substrate 1435*a* may include a flexible printed circuit board (PCB) that is semi-rigid and that includes a stiffener. Components of optical sensor 1404 may be mounted on to substrate 1435*a*. One or more control wires 1435*c* may extend proximally from optical sensor 1404 to couple optical sensor 1404 to, e.g., power sources, computing devices, and the like.

Optical sensor 1404 may include a photodetector 1437, and emitters 1436*a*, 1436*b*, and 1436*c*. Photodetector 1437 and emitters 1436 may be substantially similar to detector 137 and emitters 136 set forth above. Each emitter 1436*a-c* may be configured to radiate infrared light, or another suitable wavelength. For example, some applications may benefit from infrared light, while other applications may benefit from other wavelengths of light. For example, infrared light wavelengths may penetrate deeper into tissue while visible light provides more information regarding surface characteristics. Different wavelengths reflect back de-oxygenated/oxygenated blood differently, and there are known ratios that related to levels of oxygen, carbon dioxide and other characteristics in the tissue. While three emitters are shown in the embodiment of FIGS. 14-16, any other suitable number may be utilized. Photodetector 1437 and each of emitters 1436*a-c* may be disposed linearly along a same axis, such as, e.g., a longitudinal axis of catheter 1403. Exemplary dimensions of optical sensor 1404 are shown in FIG. 16. While certain values for each dimension are discussed below, it is contemplated that alternative dimensions also may be used. Substrate 1435 may have a length 1602 (e.g., 15 mm), and a width 1604 (e.g., 3 mm). A distalmost portion of photodetector 1437 may be disposed a distance 1606 (e.g., 1 mm) from a distalmost end of substrate 1435. A proximalmost portion of photodetector 1437 may be disposed distances 1608 (2 mm), 1610 (6 mm), and 1612 (10 mm) from distalmost portions of emitters 1436*a*, 1436*b*, and 1436*c*, respectively. It is contemplated that other suitable dimensions also may be utilized.

A lens 1438 may be disposed over optical sensor 1404 (including photodetector 1437 and each emitter 1436*a-c*). Lens 1438 may isolate optical sensor 1404 from tangential back scatter light between emitters 1436 and photodetector 1437 from substrate 1435*a*. Lens 1438 also may provide a barrier between tissue and the optical elements of optical sensor 1404. The configuration of lens 1438 and optical sensor 1404 may help enable medical device 1400 to determine tissue thickness in the body with a relatively small profile and package. Lens 1438 may be formed from plastic, glass, or another suitable material.

Photodetector 1437 may be a square-shaped photodetector having sides with a length of 2 mm, although other suitable shapes and dimensions are contemplated. Each emitter 1436 may be a square-shaped emitter having sides with a length of 1 mm, although other suitable shapes and dimensions are contemplated. In some implementations, a length of the flexible substrate is no more than 15 mm. In another embodiment, a length of the flexible substrate is no more than 11 mm.

Optical sensor 1404 may be coupled to a controller 1450 attached to a substrate 1435*b* that is substantially similar to substrate 1435*a* described above. Controller 1450 may be disposed entirely within a volume contained within catheter 1403. When controller 1450 is disposed within catheter 1403, it may have a width less than 3 mm. Alternatively, controller 1450 may be disposed external to medical device 1400, in which case, the control wires from controller 1450 to optical sensor 1404 may be attached to a flexible extension of the device.

Controller 1450 may be configured to direct and source constant current for each emitter 1436*a-c* separately, but not simultaneously, as the data acquisition may be time multiplexed during a sampling cycle. In other words, at any given time, only one of emitters 1436*a-c* may emit light. The current setting for each emitter 1436*a-c* may change due to the spatial diversity from photodetector 1437, and may be adjusted during a calibration process. Photodetector 1437 may require control of an amplification device. Since photodetector 1437 may be mostly capacitive, a trans-impedance amplifier may be used for the analog interface.

Figure 17:
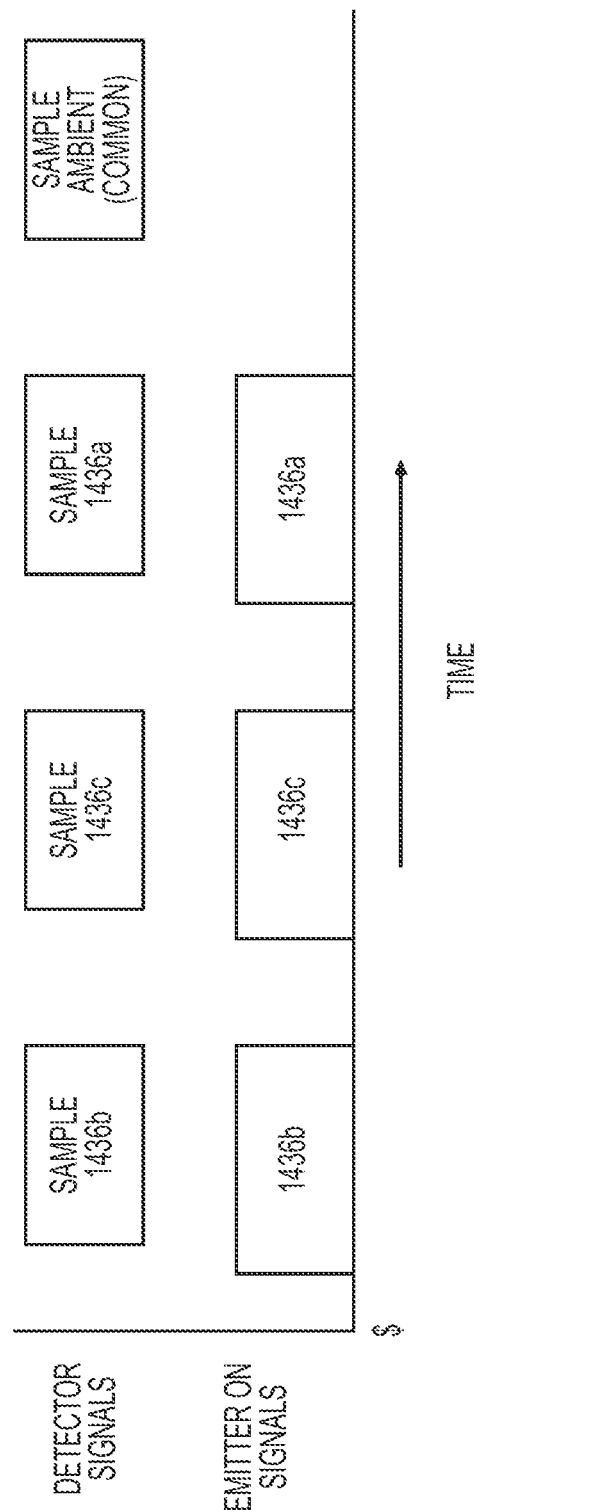
FIG. 17 is an illustration of a timing sequence of a photodetector and a plurality of emitters from the optical sensor of FIG. 14.

The spatially diverse optical sensor 1404 may be driven through three time division slots to activate each emitter 1436*a-c* separately, with a fourth time slot allowing for data acquisition when none of the emitters 1436*a-c* is activated. This fourth time slot enables the sampling of ambient light. If an operator is confident that the area being measured has no ambient light, then the fourth time slot may be skipped to reduce procedure time. This sequence is shown in FIG. 17. The acquisition of samples may be timed sequentially to enable each emitter 1436 a small period of on-ramp to allow for wavelength and temperature stabilization before a measurement is obtained by photodetector 1437. Suggested sample times could be from 50 microseconds to 200 microseconds per data acquisition. A sample period may include the complete cycle of all four periods, and may impact the overall sample rate of the signal data acquisition.

For tissue thickness measurements, 50 samples per second may be adequate, allowing for a total sample period of 20 milliseconds. This would allow for 200 microsecond emitter (LED) sampling. In order to increase data fidelity, the sample period may be increased to, e.g., up to 200 samples. In this case, the total sampling period for all four channels is 500 microseconds, allowing for emitter sampling of about 100 microseconds. A longer emitter sampling period allows for a more refined dynamic range of the analog sampling through photodetector 1437 with lower emitter current being supplied (similar to more exposure time in photography for a lower light setting).

The analog data provided by the amplifier after sampling each emitter may be converted to digital format for further processing. This disclosure contemplates any suitable type of analog to digital converter (ADC). The accuracy of the ADC may be at least comparable to an 8-bit or greater ADC to meet the measurement requirements of the applications contemplated by this disclosure.

The medical devices described with respect to FIGS. 14-17 can enable the use of emitters using a centroid wavelength of approximately 940 nm (e.g., 930-950 nm) arranged linearly apart from one another to collect a diffusion gradient of reflected and absorbed light in tissue. Evaluation of the gradient makes use of a slopes-ratio method to correlate measurements made by photodetector 1437 with tissue thickness. The ratio comprises three different vectors coming from three LED emitters (e.g., emitters 1436*a-c*) relative to a fixed photodiode (e.g., photodetector 1437). Considering the distance of the emitters 1436*a-c* from photodetector 1437, emitter 1436*a* is the closest to photodetector 1437 at a distance of two mm, emitter 1436b is mid-range relative to photodetector 1437 at a distance of six mm, and the furthest is emitter 1436c at a distance of ten mm relative to photodetector 1437.

Tissue thickness may be determined based on data collected by photodetector 1437. For example, a ratio of slopes method can be used for evaluating the short, mid and long reflective distances as shown in the formula below:

$$T_{ratio} = \frac{1436a - 1436b}{1436a - 1436c}$$

In the above equation, 1436a, 1436b, and 1436c represent values measured by photodetector 1437 in response to emissions from emitters 1436a, 1436b, and 1436c, respectively. This equation is used further in the linear model described below.

The use of different wavelengths may provide an ability to measure different skin depths. Infrared light, for example, may provide better skin depth penetration than some of the wavelengths in the visible spectrum. Other wavelengths offer different optical properties in live tissue, and may be used for other characteristics and still provide thickness measurements. Empirical results from a study show slight variations in early results using simulated tissue phantoms. The basis of certain results are from fabricated models. In a lab setup, different wavelengths were evaluated to determine different absorption and reflection patterns.

A fitted line for linear model statistical regression from data collected with an exemplary device similar to the device described by FIGS. 14-16 is shown below.

Coefficients:

TABLE 1

Statistical Curve for Collected Data

|  | Estimate | Standard Error | t value | Pr(>\|t\|) |
|---|---|---|---|---|
| Intercept | 0.891731 | 0.011087 | 80.434 | 1.43E−07 |
| Thickness | −0.017409 | 0.002181 | −7.982 | 0.00134 |

Table 1 illustrates how well the regression fits in the data. Intercept (b) and thickness (m) estimates are the coefficients for scaling according to the collected data. The significance codes are a function of the R utility to give a approximation of how valid the probability of the null hypothesis tested is. The smaller the Pr value, the higher the significance. When significance is higher, the mathematical outcome being evaluated is higher.

The residual standard error was 0.0128 on four degrees of freedom. The multiple R-squared was 0.9409, and the adjusted R-squared was 0.9262. The F-statistic was 63.71 on one and four degrees of freedom, and the p-value was 0.001335. The correlation value was −0.9700123, which measures the linear relationship between two variables. In this case, there is a negative correlation between the IR slope value and tissue thickness. As the thickness increases, IR slope value decreases (i.e., they are inversely related to each other). Both of the p-values were below 0.05 thresholds, and thus, this model was statistically significant.

Model Fitted Values

TABLE 2 shows the delta between the real values collected for each thickness measurement and the related curve fit plot.

| Thickness | Actual IR Values | Fitted IR Values |
|---|---|---|
| 1.6 | 0.869627 | 0.8638776 |
| 2.5 | 0.858604 | 0.8482098 |
| 3.0 | 0.834698 | 0.8395055 |
| 4.9 | 0.789127 | 0.8064291 |
| 6.4 | 0.773979 | 0.7803161 |
| 8.5 | 0.756061 | 0.743758 |

Linear Model $$Y = 0.891731 - 0.017409 X$$

The R-squared value was 0.9409. 94 percent represents the proportion of variation in the response variable. Thus, as tissue thickness increases, the IR slope value decreases.

Figure 18:
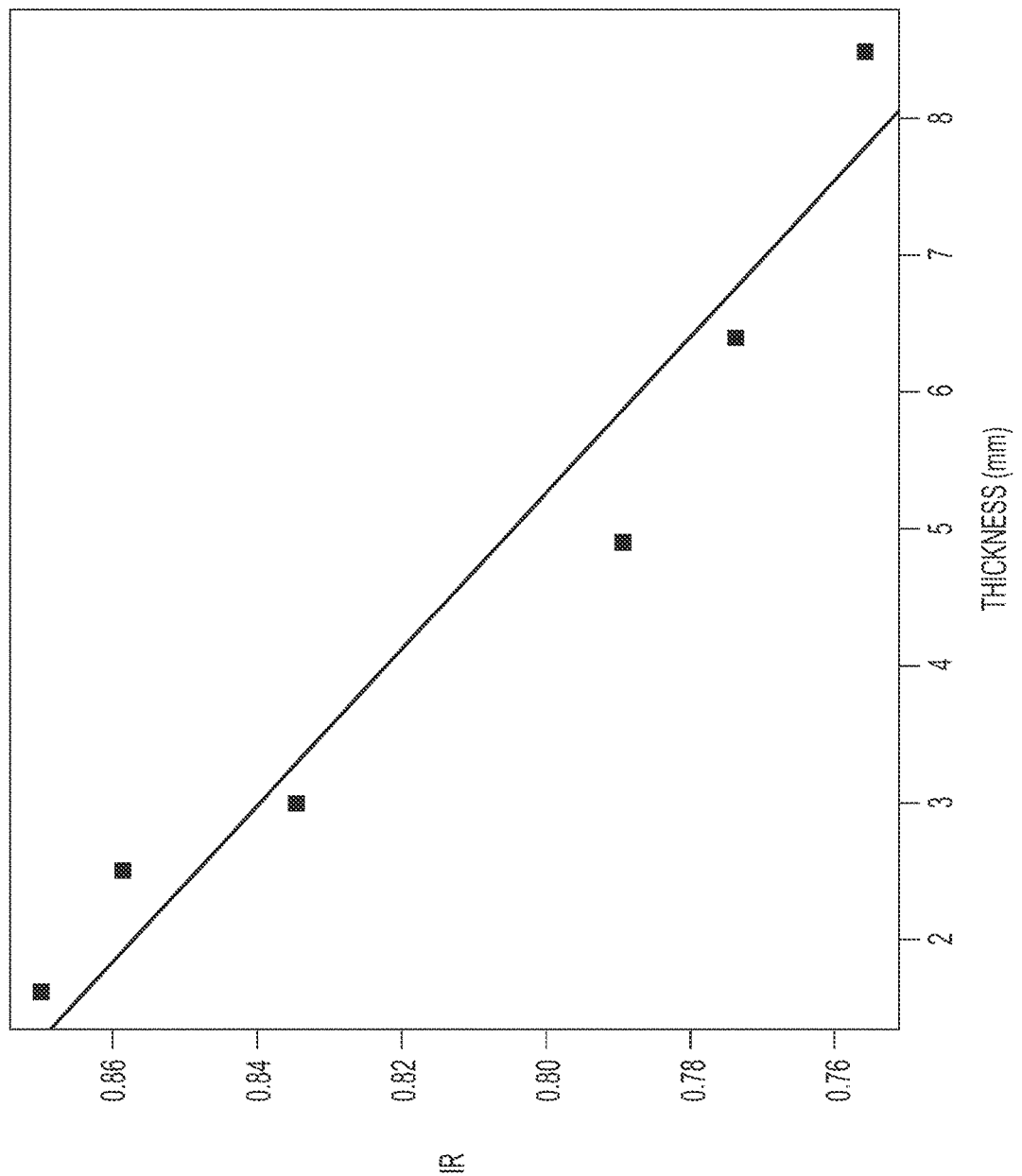
FIG. 18 is a fitted line plot regression of an experiment using an optical sensor.

The linear model is shown in FIG. 18, which is a fitted line plot regression analysis of this experiment in an SIG lab with phantom optical equivalent tissue models using slopes ratios methods.

One example translation with this dataset is:

$$\text{Thickness(mm)} = \frac{R - T_{ratio}}{k}$$

Where R is the intercept (0.8917 in this example) and k (0.01741 in this example) is the slope (negative) derived from experimental data.

The relatively slim profile of medical device 1400 also may enable internal placement of medical device 1400 though a scope using direct visualization methods. Medical device 1400 may be used to access many regions of interest in the intestinal tract (e.g., esophagus, stomach, large intestines, duodenum, and parts of the small intestines). In other examples, medical device 1400 may be used to measure thickness in a region of interest, which can then be used as a datapoint to help quantify the severity of healing or inflammation. The data can be part of an index if used with other measurements, such as, e.g., changes in perfusion, temperature, microvascular changes for severity scoring and healing of the tissue of interest. Furthermore, because optical sensor 1404 is flat, it may be used to determine tissue thickness when placed external to a patient, such as, for example, against the skin of a patient.

Those skilled in the art will understand that the medical devices set out above can be implemented in any suitable body lumen (e.g., blood vessels, the biliary tract, urological tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other implementations of the present disclosure will be apparent to those skilled in the art from consideration of the specification and practice of the implementations disclosed herein. It is intended that the specification and implementations be considered as examples only, and departures in form and detail may be made without departing from the scope and spirit of the present disclosure as defined by the following claims.

What is claimed is:

1. A medical device, comprising:
   a catheter;
   an optical sensor disposed at or adjacent to a distal end of the catheter, the optical sensor including a photodetector and one or more emitters, the photodetector and each of the one or more emitters of the optical sensor being disposed linearly along a longitudinal axis of the catheter; and
   a controller disposed within the catheter, the controller being configured to determine a thickness of tissue adjacent to the optical sensor based on input from the optical sensor;
   wherein the one or more emitters are configured to collect a diffusion gradient of reflected and absorbed light in the tissue adjacent to the optical sensor.

2. The medical device of claim 1, wherein the catheter includes a circular cross-section along a proximal portion of the catheter, and a semicircular cross-section along a distal portion of the catheter.

3. The medical device of claim 2, wherein the distal portion of the catheter includes a planar side surface and a rounded side surface, with the optical sensor disposed on the planar side surface such that the photodetector and the one or more emitters are positioned flush relative to one another on the distal portion.

4. The medical device of claim 2, wherein the catheter includes a substrate disposed over the distal portion, wherein the substrate includes a flexible printed circuit board, and the optical sensor is mounted on the substrate.

5. The medical device of claim 4, further including a lens disposed over the optical sensor, wherein the lens is configured to isolate the photodetector and the one or more emitters from tangential back scatter light between emitters and photodetectors from the substrate.

6. The medical device of claim 5, wherein the lens is configured to isolate the photodetector and the one or more emitters from the tissue adjacent to the optical sensor.

7. The medical device of claim 4, wherein the controller is mounted on the substrate and positioned flush with the photodetector and the one or more emitters.

8. The medical device of claim 1, wherein the controller is configured to correlate measurements of the gradient of reflected and absorbed light with tissue thickness via a slope-ratio.

9. The medical device of claim 8, wherein each of the one or more emitters is positioned along the planar side surface at varying linear distances from the photodetector;
   wherein the slope-ratio is at least partially based on the linear distances of each of the one or more emitters from the photodetector and the diffusion gradient collected by each of the one or more emitters.

10. The medical device of claim 1, wherein the controller is configured to activate each of the one or more emitters during a time slot that is separate from one another;
    wherein the controller is configured to separately direct current to each of the one or more emitters such that only one of the one or more emitters emits light during the time slot.

11. The medical device of claim 10, wherein the controller is configured to acquire a plurality of data samples, with each of the plurality of data samples including light detected by the photodetector during each of the time slots for the one or more emitters.

12. The medical device of claim 11, wherein the plurality of data samples acquired by the controller ranges from about 50 data samples to about 200 data samples when determining the thickness of tissue adjacent to the optical sensor.

13. A medical device, comprising:
    a catheter having a proximal end and a distal end;
    a flexible printed circuit board disposed on the distal end of the catheter;
    an optical sensor mounted on the flexible printed circuit board at the distal end of the catheter, the optical sensor including a photodetector and a plurality of emitters, the photodetector and each of the plurality of emitters are positioned in a linear arrangement relative to one another; and
    a controller configured to determine a thickness of tissue positioned adjacent to the distal end based on input from the optical sensor.

14. The medical device of claim 13, wherein the distal end of the catheter includes a half-moon shaped profile with a rounded side and a planar side, with the optical sensor mounted to the planar side.

15. The medical device of claim 13, wherein the plurality of emitters are configured to collect a diffusion gradient of light from the tissue positioned adjacent to the optical sensor, and the controller is configured to correlate measurements of the gradient of light with tissue thickness via a slope-ratio.

16. The medical device of claim 15, wherein the slope-ratio is at least partially based on a distance between each of the plurality of emitters from the photodetector and the diffusion gradient collected by each of the plurality of emitters.

17. The medical device of claim 13, wherein the controller is configured to direct current to each of the plurality of emitters during a separate time slot such that only one of the plurality of emitters emits light during each time slot.

18. The medical device of claim 17, wherein the controller is configured to acquire samples based on light detected by the photodetector during each of the time slots.

19. A medical device, comprising:
    a catheter including a proximal end, a distal end having a semicircular cross-section, and a substrate including a flexible printed circuit board disposed over the distal end;
    an optical sensor mounted on the substrate at the distal end of the catheter, wherein the optical sensor is laterally movable relative to the proximal end of the catheter, the optical sensor includes at least one photodetector and at least one emitter that are aligned linearly relative to one another along the distal end of the catheter; and
    a controller in communication with the optical sensor, the controller is configured to determine a thickness of tissue detected adjacent to the distal end of the catheter based on light detected by the optical sensor.

20. The medical device of claim 19, wherein the distal end of the catheter includes a joint that is configured to articulate, thereby bending the distal end relative to the proximal end of the catheter to move the optical sensor laterally relative to the proximal end.

* * * * *